US011932850B2

(12) United States Patent
Siegfried et al.

(10) Patent No.: US 11,932,850 B2
(45) Date of Patent: Mar. 19, 2024

(54) CANCER CHEMOPREVENTION WITH STAT3 BLOCKERS

(71) Applicant: Jill M. Siegfried, Pittsburgh, PA (US)

(72) Inventors: Jill M. Siegfried, Minneapolis, MN (US); Christian Nzinkeu Njatcha, Minneapolis, MN (US); Mariya Farooqui, Minneapolis, MN (US)

(73) Assignee: Jill M. Siegfried, LLC, Pittsburgh, PA (US)

( * ) Notice: Subject to any disclaimer, the term of this patent is extended or adjusted under 35 U.S.C. 154(b) by 7 days.

(21) Appl. No.: 17/042,708

(22) PCT Filed: Mar. 28, 2019

(86) PCT No.: PCT/US2019/024682
§ 371 (c)(1),
(2) Date: Sep. 28, 2020

(87) PCT Pub. No.: WO2019/191493
PCT Pub. Date: Oct. 3, 2019

(65) Prior Publication Data
US 2021/0139899 A1     May 13, 2021

Related U.S. Application Data

(60) Provisional application No. 62/650,892, filed on Mar. 30, 2018.

(51) Int. Cl.
| C07H 21/02 | (2006.01) |
| A61K 31/517 | (2006.01) |
| A61P 35/00 | (2006.01) |
| C07H 21/04 | (2006.01) |
| C12N 15/113 | (2010.01) |
| G01N 33/574 | (2006.01) |

(52) U.S. Cl.
CPC .......... *C12N 15/113* (2013.01); *A61K 31/517* (2013.01); *A61P 35/00* (2018.01); *G01N 33/57484* (2013.01); *C12N 2310/11* (2013.01); *C12N 2310/13* (2013.01); *C12N 2310/314* (2013.01); *C12N 2310/315* (2013.01); *C12N 2310/3183* (2013.01); *C12N 2310/3231* (2013.01); *C12N 2310/531* (2013.01); *C12N 2310/532* (2013.01); *G01N 2333/5412* (2013.01); *G01N 2333/90245* (2013.01)

(58) Field of Classification Search
CPC .......... C12N 15/113; C12N 2310/14
See application file for complete search history.

(56) References Cited

U.S. PATENT DOCUMENTS

| 6,159,694 A | 12/2000 | Karras |
| 6,727,064 B2 | 4/2004 | Karras |
| 8,623,643 B2 | 1/2014 | Karras |
| 8,722,640 B2 | 5/2014 | Grandis et al. |
| 9,062,121 B2 | 6/2015 | Grandis et al. |
| 2005/0196781 A1* | 9/2005 | Robin ............... C07H 21/02 536/23.1 |
| 2006/0293264 A1 | 12/2006 | Grandis et al. |
| 2013/0129675 A1 | 5/2013 | Priebe et al. |

FOREIGN PATENT DOCUMENTS

| WO | 2011163423 A2 | 12/2011 | |
| WO | WO 2015/077657 A2 * | 5/2015 | ........... C12N 15/113 |
| WO | 2019036509 A1 | 2/2019 | |

OTHER PUBLICATIONS

Elbashir et al. (The EMBO Journal, vol. 20, No. 23, pp. 6877-6888, 2001).*
Carpenter et al. (Cancers, 2014, 6, 897-925).*
Avalle et al. (Cytokine, 98, 2017, 42-50).*
Zhao et al. (Oncotarget, 6, 16, 2015, 14472-14487).*
Sen et al. (Clin Cancer Res, 18(18), 2012, 4986-4996).*
Kwok et al. (Human Vaccines & Immunotherapeutics, 2016, 12, 11, 2777-2789).*
Dean, N , et al., "Antisense oligonucleotide-based therapeutics for cancer", Oncogene 22, 9087-9096 (2003).
Dutta, P , et al., "Role of STAT3 in lung cancer", JAK-STAT 3(4), e999502, 9 pages (2015).
Fagard, R , et al., "STAT3 inhibitors for cancer therapy Have all roads been explored?", JAK-STAT 2(1), 1-9 (2013).
Furtek, S , et al., "Strategies and Approaches of Targeting STAT3 for Cancer Treatment", ACS Chem Biol 11, 308-318 (2016).
Gao, S , et al., "Mutations in the EGFR kinase domain mediate STAT3 activation via IL-6 production in human lung adenocarcinomas", Journal of Clinical Investigation 117(12), 3846-3856 (2007).
Grabner, B , et al., "Disruption of STAT3 signalling promotes KRAS-induced lung tumorigenesis", Nature Communications 6, 6285, 1-14 (2015).
He, G , et al., "Inhibition of STAT3- and MAPK-dependent PGE2 synthesis ameliorates phagocytosis of fibrillar β-amyloid peptide (1-42) via EP2 receptor in EMF-stimulated N9 microglial cells", Journal of Neuroinflammation 13, 296, 14 pages (2016).
Hong, D , et al., "AZD9150, a next-generation antisense oligonucleotide inhibitor of STAT3 with early evidence of clinical activity in lymphoma and lung cancer", Sci Transl Med 7(314), 314ra185, 1-13 (2015).
Juliano, R , "The delivery of therapeutic oligonucleotides", Nucleic Acids Research 44(14), 6518-6548 (2016).
Kidder, B , et al., "Stat3 and c-Myc Genome-Wide Promoter Occupancy in Embryonic Stem Cells", PLoS One 3(12), e3932, 14 pages (2008).
Klein, J , et al., "STAT3 Oligonucleotide Inhibits Tumor Angiogenesis in Preclinical Models of Squamous Cell Carcinoma", PLoS One 9(1), e81819, 10 pages (2014).

(Continued)

Primary Examiner — Amy H Bowman
(74) Attorney, Agent, or Firm — David G. Oberdick; Chiara F. Orsini

(57) ABSTRACT

Described herein are compositions that inhibit/degrade STAT3, and methods of using such compositions for chemoprevention of non-small cell lung cancer (NSCLC).

8 Claims, 20 Drawing Sheets

Specification includes a Sequence Listing.

(56) References Cited

OTHER PUBLICATIONS

Lee, H., et al., "Drug Resistance via Feedback Activation of Stat3 in Oncogene-Addicted Cancer Cells", Cancer Cell 26, 207-221 (2014).

Leong, P., et al., "Targeted inhibition of Stat3 with a decoy oligonucleotide abrogates head and neck cancer cell growth", PNAS 100(7), 4138-4143 (2003).

Njatcha, C., et al., "Prevention of tobacco carcinogen-induced lung tumor development by a novel STAT3 decoy inhibitor", Cancer Prev Res 13(9), 735-746 (2020).

Njatcha, C., et al., "STAT3 Cyclic Decoy Demonstrates Robust Antitumor Effects in Non-Small Cell Lung Cancer", Mol Cancer Ther 17(9), 1917-1926 (2018).

Njatcha, C., et al., "Targeting the EGFR/STAT3 axis in NSCLC with resistance to EGFR tyrosine kinase inhibitors using an oligonucleotide-based decoy", Proceedings of the American Association for Cancer Research (2017) vol. 58: p. 1048, Abstract # 4101, Apr. 2017. Available online Mar. 31, 2017.

Patent Cooperation Treaty, International Searching Authority, Search Report and Written Opinion for PCT/US2019/024682, 10 pages, dated Jun. 19, 2019.

Schlessinger, K., et al., "Malignant Transformation but not Normal Cell Growth Depends on Signal Transducer and Activator of Transcription 3", Cancer Res 65(13), 5828-5834 (2005).

Seethala, R., et al., "Immunohistochemical Analysis of Phosphotyrosine Signal Transducer and Activator of Transcription 3 and Epidermal Growth Factor Receptor Autocrine Signaling Pathways in Head and Neck Cancers and Metastatic Lymph Nodes", Clin Cancer Res 14(5), 1303-1309 (2008).

Sen, M., et al., "First-in-Human Trial of a STAT3 Decoy Oligonucleotide in Head and Neck Tumors: Implications for Cancer Therapy Malabika Sen1,", Cancer Discov 2(8), 694-705 (2012).

Sen, M., et al., "Systemic Administration of a Cyclic Signal Transducer and Activator of Transcription 3 (STAT3) Decoy Oligonucleotide Inhibits Tumor Growth without Inducing Toxicological Effects", Mol Med 20, 46-56 (2014).

Yao, Z., et al., "TGF-beta IL-6 axis mediates selective and adaptive mechanisms of resistance to molecular targeted therapy in lung cancer.", Proc Natl Acad Sci U S A 107 (35), 15535-15540 (2010).

Zhou, J., et al., "Myeloid STAT3 Promotes Lung Tumorigenesis by Transforming Tumor Immunosurveillance into Tumor-Promoting Inflammation", Cancer Immunol Res 5(3), 257-268 (2017).

* cited by examiner (*P = .019)

CANCER CHEMOPREVENTION WITH STAT3 BLOCKERS

CROSS REFERENCE TO RELATED APPLICATION

This application claims priority to U.S. Provisional Application No. 62/650,892 filed on 30 Mar. 2018, which is incorporated by reference herein.

GOVERNMENT FUNDING

This invention was made with government support under F31-CA213982 awarded by the National Institutes of Health. The government has certain rights in the invention.

SUBMISSION OF SEQUENCE LISTING

The content of the following submission on ASCII text file is incorporated herein by reference in entirety: a computer readable form (CRF) of the Sequence Listing (file name: 09531_462WO1_SL.txt, created: Mar. 25, 2019, size 5,624).

FIELD OF THE INVENTION

Described herein are compositions that inhibit and/or degrade STAT3, and methods of using such compositions for the cancer chemoprevention of STAT3-related disorders, for enhancing the immune system's ability to reject cancer, and for using biomarkers to monitor the biological activity of compositions that inhibit and/or degrade STAT3.

BACKGROUND

Signal transducer and activator of transcription 3 (STAT3) mediates the expression of a variety of genes in response to cell stimuli and thus plays a key role in several cellular processes such as cell growth and apoptosis. Studies of the Janus kinases (JAKs) and signal transducers and activators of transcription (STATs) signaling have uncovered highly conserved programs linking cytokine signaling to the regulation of essential cellular mechanisms such as proliferation, invasion, survival, inflammation and immunity. Inhibitors of the JAK/STAT pathway are used for treatment of autoimmune diseases, such as rheumatoid arthritis or psoriasis. Aberrant JAK/STAT signaling has been identified to contribute to cancer progression and metastatic development. Deregulation of the STAT3 activity has been shown in many malignancies, including breast, head and neck, lung, prostate, pancreas, ovarian and brain cancers and melanoma.

Chemoprevention is distinguishable from treatment of cancer; in the former cancerous lesions may not be present. Treatment and chemoprevention may target different patient populations. There is a need to develop preventative treatment options for patients at risk of developing cancer, including non-small cell lung cancer (NSCLC). Safe and effective chemoprevention agents have enormous potential to improve human health. Effective preventive therapy has been demonstrated convincingly in cardiovascular disease, where modifiable risk factors such as high blood pressure and elevated cholesterol levels were identified and targeted for pharmacological management. The result has been the reduction of both the morbidity and mortality associated with heart disease. For some cancers, the promise of chemoprevention has already been realized. Recurrence of breast cancer is being reduced with tamoxifen therapy, and the incidence of colon cancer is being reduced significantly with NSAIDs.

Lung cancer remains the leading cause of cancer-related mortality in the United States, representing more than 25% of all cancer deaths, which is largely attributed to the dismal survival of stage IV disease (Siegel R L, et al, Cancer Statistics: 2017. CA *Cancer J Clin* (2017) 67:7-30; Jemal A. et al *J Natl Cancer Inst* (2017) 109 (9); Torre L A, et al, *Cancer Epidemiol Biomarkers Prev* (2016) 25:16-27). In NSCLC, which accounts for 85% of all lung cancer cases (Chen Z, et al *Nat Rev Cancer* (2014) 14:535-46), patients are stratified based on genetic alterations in the tumor, which serve as predictive biomarkers for targeted therapy. Patients with somatic epidermal growth factor receptor (EGFR) mutations (such as the L858R point mutation and exon 19 deletions) initially respond to EGFR tyrosine kinase inhibitors (TKIs), but eventually develop acquired resistance through new mutations such as the EGFR T790M substitution. The majority of patients without EGFR mutation, including those who lack alterations in other "drivers", are intrinsically resistant to EGFR TKIs (Gainor J F, et al, *J Clin Oncol* (2013) 31:3987-96).

Constitutively activated STAT3 plays a critical role NSCLC progression by mediating proliferation and survival. The activation of STAT3 in normal cells is transient, making it an attractive target for NSCLC therapy. STAT3, a transcription factor that controls important growth-promoting genes, is a key mediator of receptor tyrosine kinase (RTK) downstream signaling. In NSCLC, STAT3 activation is correlated with heightened EGFR signaling, as well as increased c-Met and IL6 receptor signaling. STAT3 inhibition could also potentially be effective when combined with inhibitors of other RTKs, either in tumors with addiction to a specific pathway like FGFR or c-Met, or in patients with acquired EGFR TKI resistance due to upregulation of those pathways. In addition to promoting tumor growth directly, STAT3 also is active in promoting immunosuppression.

STAT3 was often activated during in vitro induction of resistance to the EGFR inhibitor erlotinib (TARCEVA®, Genentech), as the result of feedback up-regulation of multiple other kinases, suggesting that increased STAT3 activity could commonly occur in response to drugs that target kinases (Lee H-J. et al *Cancer Cell* (2014) 26:207-221). During lung cancer progression, STAT3 is also often constitutively active, upregulating the expression of important target genes necessary for cellular proliferation, survival, and evasion of cell death (Dutta P, et al, JAK-STAT (2015) 3 (4), e999503. 2015 Jan. 20). As a point of convergence for many signaling pathways that are dysregulated during NSCLC progression, STAT3 mediates adaptive mechanisms of resistance to molecular targeted therapy in NSCLC, such as induction of epithelial-to-mesenchymal transition by IL-6 in response to erlotinib (Yao Z, et al, *Proc Natl Acad Sci USA* (2010) 107:15535-40: Gao S P, et al, *J Clin Invest* (2007) 117:3846-56). Since STAT3 plays a critical role in malignant cell transformation, but is not essential for normal cell growth (Schlessinger K, et al, *Cancer Research* (2005) 65: 5828-5834), it is potentially a prime therapeutic target for cancer treatment or cancer chemoprevention.

STAT3 is a critical downstream mediator of tumor progression in NSCLC. As a transcription factor that regulates the expression of multiple target genes, STAT3 also relays signals through multiple receptor and non-receptor tyrosine kinases, including EGFR, IL-6R, and SRC. The key role of STAT3 in mediating proliferation and suppressing apoptosis in NSCLC makes it a prime target for therapeutic intervention. Efforts to apply STAT3 inhibition in the clinical setting have been limited due to a paucity of potent and selective inhibitors (Darnell J E. (2005) Nat. Med. 11:595-6; Chang, N. et al, Mol. and Cellular Endocrin. (2017) 451:53-65; Pranabananda. D. et al, JAK-STAT. (2014) 3(4): e999503; Everardo, M. et al, Journal of Skin Cancer, vol. 2013, Article ID 684050, 10 pages, 2013. doi:10.1155/2013/684050; Fagard, R., et al (2013) JAK-STAT 2(1) e22882; Furtek S L, et al, ACS Chem Biol (2016) 11:308-18). Previous approaches to inhibit STAT3 include RNA interference, peptidomimetics to prevent dimerization, and blockers of the STAT3 SH2 domain to prevent activation. STAT3 decoy oligonucleotides have been reported (Sen M, et al, Cancer Discov (2012) 8:694-705; US 2006/0293264: U.S. Pat. Nos. 8,722,640; 9,062,121). A STAT3 anti-sense oligonucleotide developed by ISIS/Eli Lilly showed low clinical activity, due to incomplete downregulation of STAT3 gene expression. Most currently available STAT3 inhibitors either target upstream kinases, lack specificity, or require exceptionally high concentrations to achieve STAT3 inhibition. Previous STAT3 oligonucleotide decoys were unstable (Castanotto D, et al. Curr Opin Oncol (2014) November: 26:584-589; Dean N M, et al, Oncogene (2003) 22:9087-96) and small molecule STAT3 inhibitors proved relatively ineffective. The ability of non-phosphorylated STAT3 to function as an active dimer (Timofeeva O A. et al, J Biol Chem (2012) 287:14192-14200; Yang J, et al, Cancer Res (2005) 65:939-47) also may limit the ability of kinase inhibitors to completely block STAT3 action.

SUMMARY

An aspect of the invention is a method for the chemoprevention of cancer by administering to a patient in need or at risk a therapeutically-effective dose of a STAT3 Blocker.

An aspect of the invention provides a means for chemoprevention using a STAT3 Decoy oligonucleotide, STAT3 antibody. STAT3 antisense, STAT3 locked nucleic acid. STAT3 aptamer, STAT3 small molecule inhibitor (as used herein "Blocker") or STAT3 degrader (as used herein "Degrader") following exposure to any generally recognized carcinogenic or cytotoxic agent/agents. FIG. 1 shows an exemplary mechanism of action where the STAT Decoy binding to pSTAT3 and blocking STAT3 dimers from binding DNA. In FIGS. 6B and 6C below, the ability of STAT3 Decoy to cause p-STAT3 to degrade is demonstrated.

Another aspect of the invention is a means for chemoprevention using a STAT3 Blocker/Degrader targeting patient populations otherwise at elevated risk of developing cancer, including without limitation, due to genetic conditions, immunocompromised status, comorbidities, medical history (including, prior treatment for cancer and presently in remission), prior treatment with or exposure to chemotherapeutic agents, commitment treatment with chemotherapy and/or radiation, prior exposure to or treatment with cytotoxic agents, prior treatment with or exposure to radiation or radon, social history, or family history.

An aspect of the invention is the use of a cyclic oligonucleotide as a specific and potent STAT3 inhibitor to inhibit the growth of lung tumors with or without the T790M mutation or with or without intrinsic resistance to EGFR TKIs, by targeting Signal Transducer and Activator of Transcription 3 (STAT3).

An aspect of the invention is a STAT3 Blocker/Degrader oligonucleotide.

The compositions of the invention target STAT3.

Two other aspects of the invention are two potential biomarkers (detection of the cytokine interleukin-6 (IL6) and the enzyme cyclo-oxygenase 2 (COX2) [or products of COX2 activity such as prostaglandin E2IPGE2]) that can detect biological activity of a STAT3 inhibitor/blocker/degrader in blood products, in cells, in tissues or in the whole body.

Another aspect of the invention is the use of a STAT3 inhibitor/blocker/degrader as a means to enhance the activity of cells of the innate and/or adaptive immune system to reject cancerous cells in the body, to augment the activity of any cancer immunotherapies that are developed to increase the activity of cells in the innate and/or acquired immune system to attack and reject cancerous cells in the body.

Another aspect of the invention is a method of measuring one or more markers selected from IL6, COX2, and $PGE_2$ as a means to detect biological activity of a STAT3 Blocker/Degrader in patients undergoing therapy or chemoprevention.

DETAILED DESCRIPTION

Figure 1:
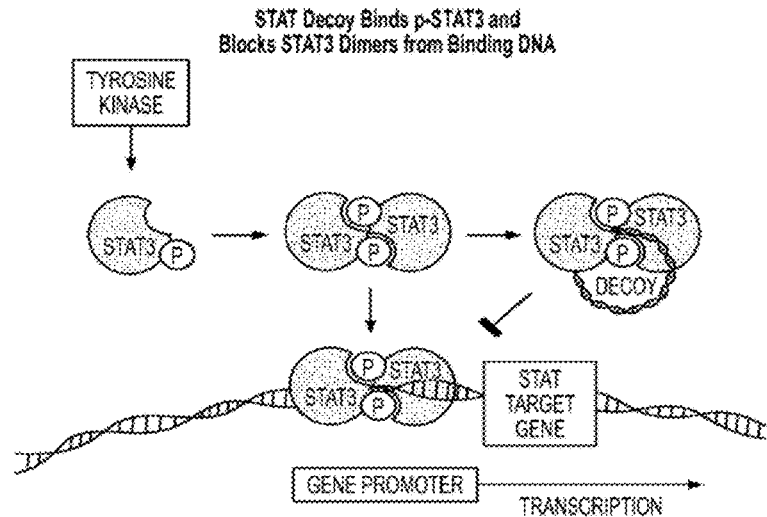
FIG. 1 shows an exemplary mechanism of action where the STAT Decoy binds to pSTAT3 and blocks STAT3 dimers from binding DNA.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. Unless otherwise defined, all technical and scientific terms used herein have the same meaning as commonly understood by one of ordinary skill in the art to which this invention belongs.

Definitions

The term "cancer chemoprevention" refers to the administration of a medication (natural, synthetic, or biological chemical agents) or a naturally occurring substance such as a nutrient or biological molecule for the purpose of reversing, suppressing, or preventing (including lowering the risk of) carcinogenic progression to invasive cancer.

The term "oligonucleotide" refers to a short DNA or RNA molecule comprised of nucleotides, A, G, C, and T. Nucleotides are organic molecules that serve as the monomer units for forming the nucleic acid polymers deoxyribonucleic acid (DNA) and ribonucleic acid (RNA), both of which are essential biomolecules in all life-forms. Nucleotides are the building blocks of nucleic acids: they are composed of three subunit molecules: a nitrogenous base, a five-carbon sugar (ribose or deoxyribose), and at least one phosphate group. Oligonucleotides readily bind, in a sequence-specific manner, to their respective complementary oligonucleosides, DNA, or RNA to form duplexes or hybrids of a higher order. Antisense oligonucleotides are single strands of DNA or RNA that are complementary to a chosen sequence. In the case of antisense RNA they prevent protein translation of certain messenger RNA strands by binding to them. Antisense DNA can be used to target a specific, complementary (coding or non-coding) RNA.

"Carcinogenic" agents are cytotoxic agents that include tobacco smoke, benzene, vaping particulates, asbestos, or some combination thereof, and including an agent on a public list of such agents maintained by the American Cancer Society. The carcinogenic agent may be cisplatin, tamoxifen, other chemotherapeutic, or combination of multiple chemotherapeutics. In still other embodiments, the carcinogenic agent is any type of radiation exposure, including radon, alone or in combination with other carcinogenic and/or chemotherapeutic agents.

The terms "treat", "treating", and "treatment" refer to therapeutic treatment, wherein the object is to slow down (lessen) or reverse an undesired physiological change, disease, condition or disorder, such as the development or spread of an infection, arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, including reduction in or reversal of preneoplastic changes, amelioration or palliation of the disease state, and remission (whether partial or total), whether detectable or undetectable. "Treatment" can also mean prolonging survival as compared to expected survival if not receiving treatment. Those in need of treatment include those with the condition or disorder or those who are at risk for the disorder.

The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein, or (iv) prevents or reverses pre-cancerous change or changes (preneoplasia) that do not medically qualify as a malignant change.

The term "alkylene" by itself or as part of another substituent means a divalent radical derived from an alkane, such as —$CH_2CH_2CH_2CH_2CH_2$—.

The term "biomarker" means a measurable biological substance that can be extracted from bodily fluid or tissues that can detect the biological activity of a drug.

The term "cancer immunotherapy" means therapies that are developed to enhance the activity of cells in the innate and/or acquired immune system to attack and reject cancerous cells in the body.

STAT3 Blockers

The STAT3 Blocker can be any type of inhibitor or blocking agent of STAT3, whether targeting STAT3 mRNA, STAT3 monomer, phosphorylated STAT3, acetylated STAT3, activated STAT3, STAT3 homodimer, or STAT3-STAT1 heterodimer. It includes any agent that degrades the STAT3 protein, in either its native or activated state, especially through the ubiquitin proteasome system.

In some embodiments, the STAT3 Blocker/Degrader comprises an oligonucleotide that is termed a Decoy, or an analog thereof.

In some embodiments, the STAT3 BlockerDegrader comprises an oligonucleotide having the sequence:

5'-(N$^6$)$_n$CAN$^1$TTCN$^2$CN$^3$TN$^4$AN$^5$TC-(N$^7$)$_m$-3' (SEQ ID NO: 15)

wherein N$^3$ is G: N$^1$, N$^2$, N$^4$, and N$^5$ are A, T, G or C; and one or more of the following conditions (i)-(v) are met:
- (i) N$^1$ is T; N$^2$ is C; N$^4$ is A; N$^5$ is A; and N$^6$ and N$^7$ are independently selected from A, T, G or C, and n and m are independently selected from an integer from 0 to 50;
- (ii) the first end of a first strand is joined to a first end of the second strand by a hexa-ethyleneglycol spacer;
- (iii) the second end of the first strand is joined to a second end of the second strand by a hexa-ethyleneglycol spacer;
- (iv) the oligonucleotide binds to STAT3 protein under physiologic conditions and interferes with STAT3 binding to its target sequence and may cause phospho-STAT3 to be degraded; and
- (v) the oligonucleotide has a serum half-life of greater than about 4 hours.

In some embodiments, the Decoy is comprised of sense and antisense oligonucleotides forming a double-stranded duplex.

In some embodiments, the Decoy is a single stranded oligonucleotide with complete or partial self-complementarity.

In some embodiments, the Decoy is an oligonucleotide having any of the following structures (or analog thereof) (SEQ ID NOS 1-4 and 16, respectively, in order of appearance):

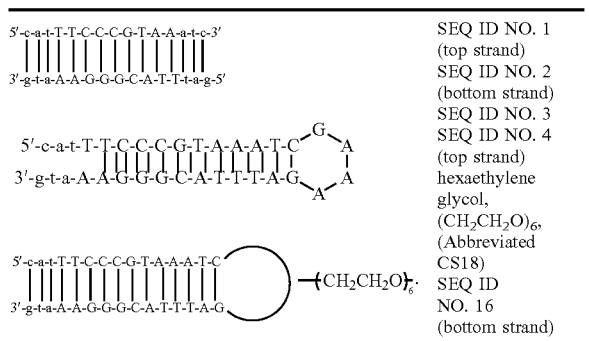

| | |
|---|---|
| | SEQ ID NO. 1 (top strand) |
| | SEQ ID NO. 2 (bottom strand) |
| | SEQ ID NO. 3 |
| | SEQ ID NO. 4 (top strand) hexaethylene glycol, (CH$_2$CH$_2$O)$_6$, (Abbreviated CS18) |
| | SEQ ID NO. 16 (bottom strand) |

In some embodiments, the Decoy comprises one or more sequences selected from the following:

```
                              SEQ ID NO: 1
5' CAT TTC CCG TAA ATC 3'

SEQ ID NO: 2
5' GAT TTA CGG GAA ATG 3'

SEQ ID NO: 3
5' CAT TTC CCG TAA ATC GAA AGA TTT

ACG GGA AAT G 3'

SEQ ID NOS: 4 and 16
5' CAT TTC CCG TAA ATC XGA TTT ACG

GGA AAT G 3'
``` where X is a hexaethyleneglycol, —(CH$_2$CH$_2$O)$_6$ spacer.

In some embodiments, the Decoy is comprised of one or more internucleotide phosphate analogs, selected from phosphorothioate, phosphoramidate, and alkylphosphonate.

In some embodiments, the STAT3 Decoy is CS3D, a self-complementary, cyclized oligonucleotide having the structure (SEQ ID NOS 4 and 16, respectively): CS3D (Cyclic STAT3 Decoy)

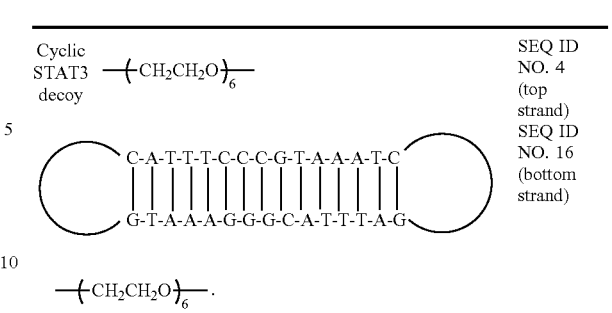

| | |
|---|---|
| Cyclic STAT3 decoy | SEQ ID NO. 4 (top strand) |
| | SEQ ID NO. 16 (bottom strand) | hexaethylene glycol (CH$_2$CH$_2$O)$_6$, abbreviated CS18
hexaethylene glycol (CH$_2$CH$_2$O)$_6$, abbreviated CS18
with two hexaethylene glycol spacers (U.S. Pat. Nos. 9,062,121; 8,722,640; Sen M, et al, *Cancer Discov* (2012) 8:694-705).

Figure 2:
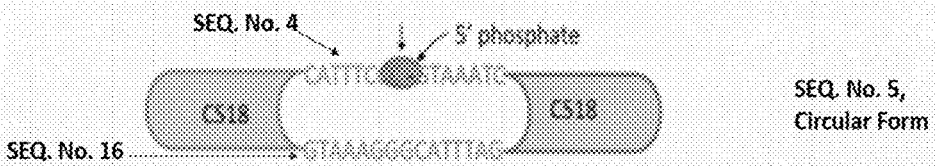
FIG. 2 shows CS3D, an exemplary embodiment of a cyclic oligonucleotide STAT Decoy with the forward and reverse STAT3 DNA consensus sequence and the cyclic structure after ligation. CS18=hexaethyleneglycol-$(CH_2CH_2O)_6$.

In some embodiments, the STAT3 Decoy is a cyclized oligonucleotide shown in the bottom half of FIG. 2, an exemplary embodiment of a cyclic oligonucleotide STAT Decoy with the forward and reverse STAT3 DNA consensus sequence. CS18=hexaethyleneglycol –(CH$_2$CH$_2$O)$_6$. In other embodiments, the STAT3 Decoy is a linear oligonucleotide as shown in the top half of FIG. 2, which is SEQ. ID. NO. 5. Also as shown in FIG. 2, the oligonucleotide CS3D consists of DNA SEQ. No. 5 linked to two hexaethylene glycol (CS18) moieties (CH$_2$CH$_2$O)$_6$. SEQ No. 5 contains both the forward DNA SEQ. No. 4 and the reverse DNA SEQ. No. 16. When ligated, the CS18 moieties are flexible and allow SEQ. No. 4 and SEQ. No. 16 to hybridize, forming a circular (cyclic) double-stranded DNA oligonucleotide.

In some embodiments, the STAT3 Decoy structure comprises a carbon spacer and receptor ligand. In some embodiments, the receptor ligand helps to target delivery of the oligonucleotide to a certain receptor. In one embodiment the STAT3 Decoy structure comprising a carbon spacer and ligand receptor is of the form (or analog thereof) (SEQ ID NOS 17, 4 and 16, respectively):

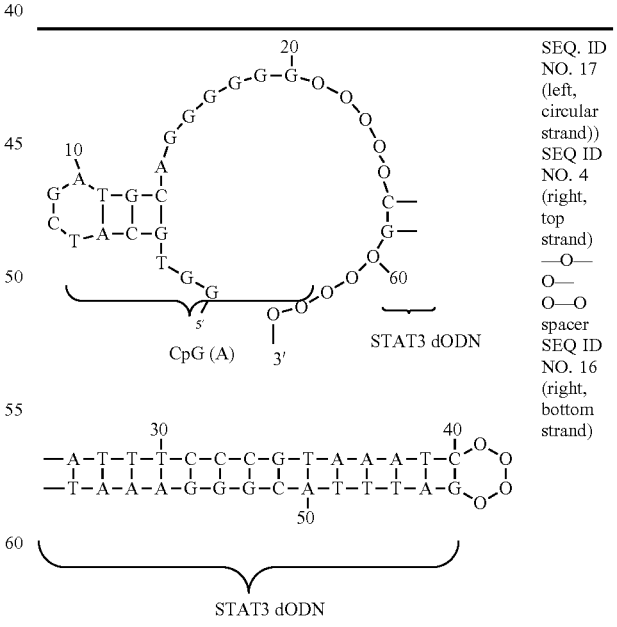

| | |
|---|---|
| | SEQ. ID NO. 17 (left, circular strand)) |
| | SEQ ID NO. 4 (right, top strand) |
| | —O— O— O—O spacer |
| | SEQ ID NO. 16 (right, bottom strand) | wherein o is a spacer moiety independently selected from C$_1$-C$_{12}$ alkylene, and —(CH$_2$CH$_2$O)$_n$— where n is 1 to 6, and —CH$_2$CH$_2$OP(O$_3$)—.

In some embodiments, the STAT3 Blocker is antisense RNA. In some embodiments, the STAT3 Blocker is AZD-9150 (ISIS 481464) or analog thereof (Hong, D. et al, Sci Transl Med. (2015) November 18; 7(314):314ra185) which has the following structure:

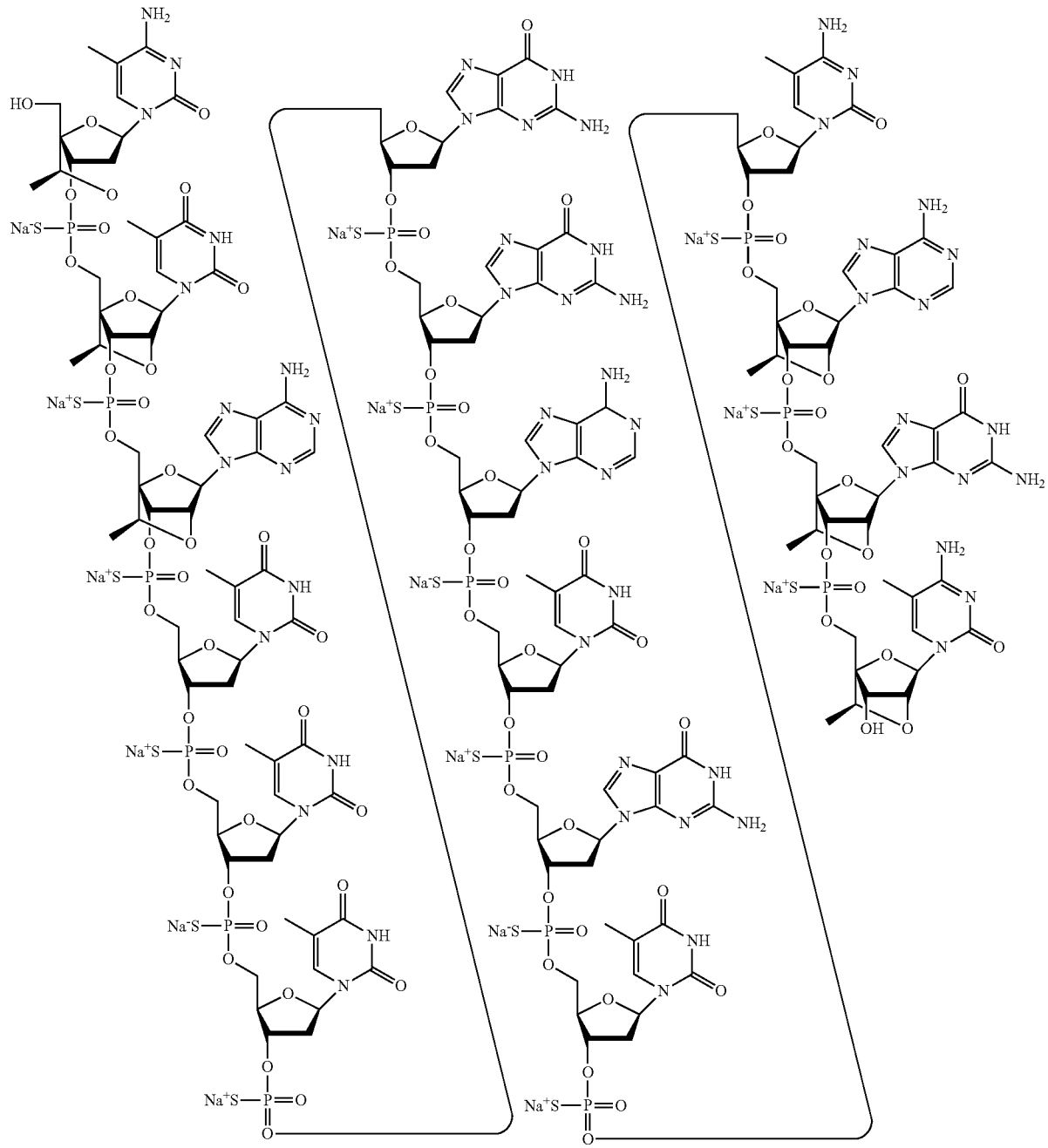

AZD-9150

In some embodiments, the STAT3 Blocker is a small molecule inhibitor such as, napabucasin, WP 1066, WP 1120, WP 1732, or analog thereof.

Not to be limited to a particular mechanism-of-action, FIG. 1 shows a DNA-based STAT3 decoy binding to pSTAT3 and blocking STAT3 dimers from binding DNA. The decoy may dampen these effects by reducing STAT3-dependent activity of myeloid-derived suppressor cells (MDSCs) and pro-tumor macrophages that promote lung cancer, suggesting STAT3 blockade could enhance immunotherapies. This approach prevents STAT3 dimers from binding their DNA promoter elements, effectively blocking the ability of activated STAT3 to induce gene transcription. Complementary oligonucleotides that mimic the DNA sequence found in the promoter regions of STAT3-responsive genes were prepared and tested.

By focusing on inhibiting the active form of STAT3 rather than blocking all STAT3 molecules, it may be easier to achieve blockade of STAT3 signaling. The oligonucleotides serve as a competitive sink for active STAT3 dimers, reducing transcription of STAT3 target genes like c-Myc. A first-generation linear decoy was very effective at blocking cancer cell growth in vitro but could not be given systemically. CS3D, an improved, second-generation version of the decoy (FIG. 2) has been produced that is thermally stable, by creating complementary oligonucleotides with two hexaethyleneglycol spacers (CS18) placed between one of the complementary sequences to allow for the production of a cyclic double-stranded DNA upon ligation with ligase.

The cyclic STAT3 decoy (CS3D) was shown to be active after systemic administration, and to have anti-tumor effects in human head and neck cancer xenografts after IV injection. Toxicology studies in mice showed no significant effects on body weight, organ histology, or clinical chemistry at repeated decoy doses up to 100 mg/kg. The novel mechanism of action combined with the stability of the circularized STAT3 decoy and its low toxicity are favorable features for clinical application. In all experiments with the STAT3 decoy, activity is compared to a mutant version with a T-A base pair replacing a G-C base pair at position 9, differing by the two nucleotides in the base pair. The mutant form (CS3M) is unable to bind STAT3 and is biologically inactive (Leong et al., *Proc Natl Acad Sci USA* (2003) 100:4138-4143).

The precycliized sequrnces of CS3D and CS3are as follow:

| | | |
|---|---|---|
| CS3D | 5' Phos GTA AAT C(CS18)GA TTT ACG GGA AAT G(CS18)CA TTT CCC 3' | SEQ ID NO. 5 with 2 $(CH_2CH_2O)_6$ hexaethyleneglycol spacers (abbreviated CS18) |
| CS3M | 5' Phos TTA AAT C(CS18)GA TTT AAG GGA AAT G (CS18)CA TTT CCC 3' | SEQ ID NO. 6 with 2 $(CH_2CH_2O)_6$ hexaethyleneglycol spacers (abbreviated CS18) | where (CS18) is a hexaethyleneglycol, $—(CH_2CH_2O)_6$ spacer.

A decoy approach was utilized by circularizing (through ligation) a double-stranded oligonucleotide containing a 15 base-pair sequence corresponding to the STAT3 response element (Leong P L, et al, *Proc Natl Acad Sci USA* (2003) 100:4138-43). The circular molecule was produced through the inclusion of two hexaethyleneglycol spacers that provide flexibility, and upon ligation becomes a thermally stable cyclic double-stranded oligonucleotide (Sen M, et al, *Cancer Discov* (2012) 8:694-705). The cyclic STAT3 decoy (CS3D) was compared to a mutant inactive control (CS3M) molecule that differs from the active compound by a single base-pair and lacks binding to the STAT3 protein. This allows an assessment of the specificity of CS3D to block STAT3's ability to regulate cellular functions. The STAT3 decoy was previously shown to decrease luciferase activity in cells expressing a luciferase reporter gene under the control of the STAT3 consensus sequence, and to competitively bind to activated STAT3 protein (pSTAT3) in comparison to the mutated version, which showed no affinity for pSTAT3 protein.

The decoy approach allows STAT3 dimers to preferentially interact with the oligonucleotide, acting as a molecular sink to competitively inhibit binding of the dimer to the promoters of STAT3 target genes. This approach has demonstrated antitumor efficacy in head and neck squamous cell carcinoma models (HNSCC) (Sen M, et al, *Mol Med* (2014) 20:46-56; Klein J D, et al, *PLoS ONE* (2014) 9(1): e81819. doi:10.1371/journal.pone.0081819), and the ligated circularized decoy exhibits greater potency when injected in vivo compared to linear versions.

Wild-Type and Mutant EGFR NSCLC Cells Exhibit Similar Sensitivity to the STAT3 Decoy (CS3D)

Figure 3A:
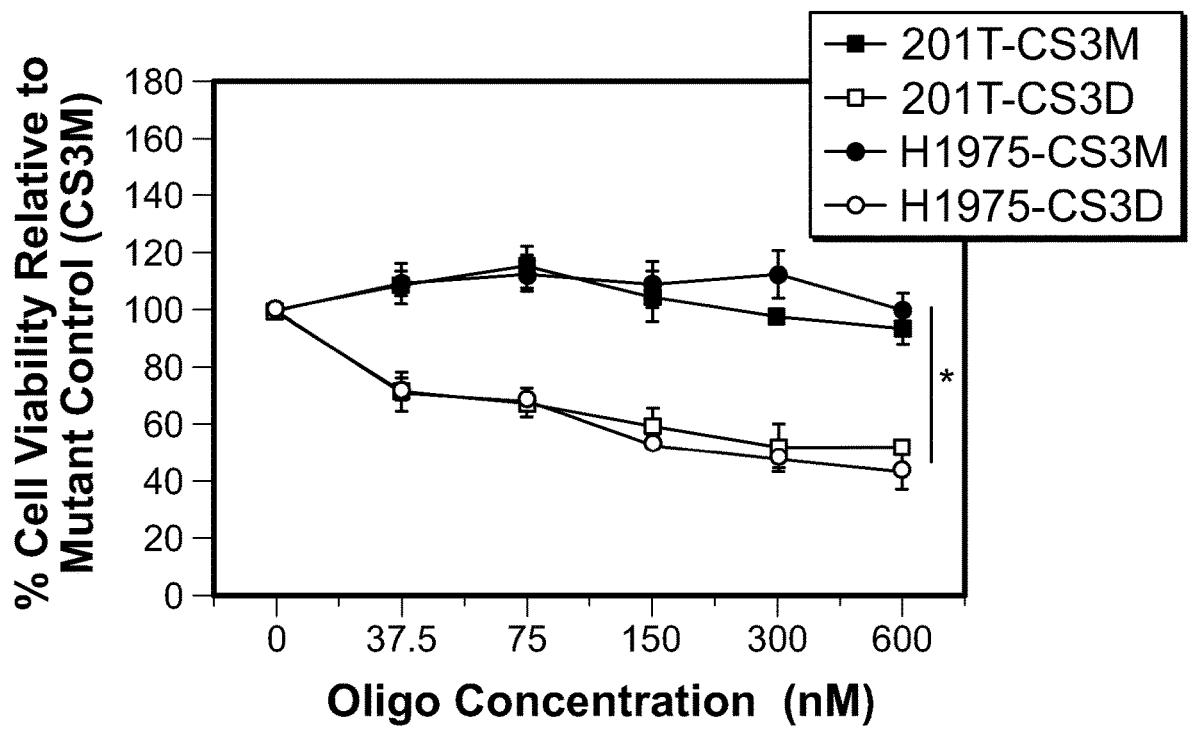
FIG. 3A shows the effects of the cyclic STAT3 decoy CS3D relative to mutant control CS3M on in vitro cell viability. NSCLC cell lines (201T and H1975) were transfected with CS3D or CS3M (cyclic STAT3 mutant decoy) at concentrations ranging from 0 nM to 600 nM.
Figure 3B:
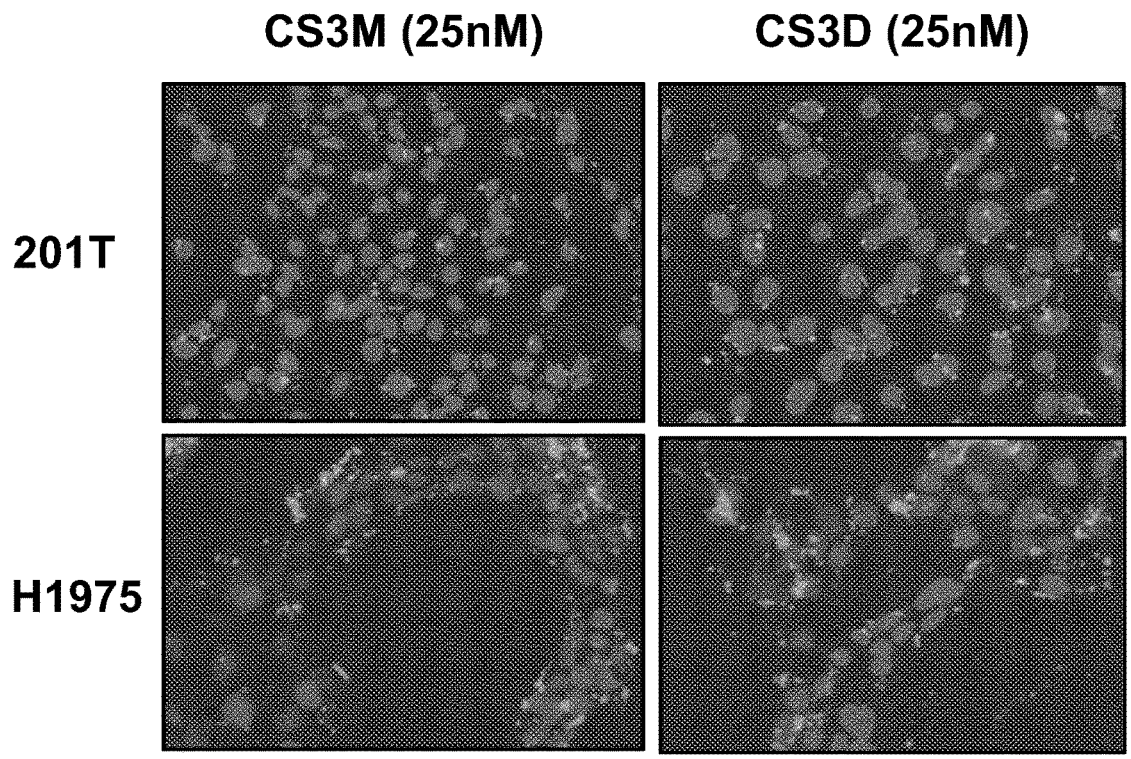
FIG. 3B shows uptake of fluorescein-labeled CS3D (cyclic STAT3 decoy) by NSCLC in vitro.

CS3D (compared to CS3M) is active in NSCLC cell culture, reducing viability and colony formation, and increasing apoptosis (Njatcha et al, *Proceedings of the American Association for Cancer Research* (2017) Volume 58: page 1048, Abstract #4101, April 2017. Available online Mar. 31, 2017). FIG. 3A shows the effects of the cyclic STAT3 decoy CS3D relative to mutant control CS3M on in vitro cell viability. NSCLC cell lines (201T and H1975) were transfected with CS3D or CS3M (cyclic STAT3 mutant decoy) at concentrations ranging from 0 nM to 600 nM. Using MTS assays, cell viabilities were assessed 72 hours later. Three independent experiments were performed, using 24-well plates and 4 wells/concentration. One 4-hr transfection of ligated CS3D using Lipofectamine (Invitrogen) caused significant is reduction in viability by MTS assay compared to CS3M in 4 NSCLC cell lines tested (Table 1). The IC50 for CS3D was approximately 300 nM in each NSLCC cell line, regardless of EGFR or KRAS mutation status. CS3M had no appreciable effect. In comparison, the IC50 for CS3D in normal lung fibroblasts and human bronchial epithelial cells was 30 nM, 100-fold higher. This agrees with toxicology studies in mice showing no appreciable changes in blood chemistry, weight or organ structure with CS3D dosing. FIG. 3B shows uptake of fluorescein-labeled CS3D (cyclic STAT3 decoy) by NSCLC in vitro. Confocal imaging 24 hours post-transfection shows intracellular localization of CS3M or CS3D in 201T and H1975 cells.

TABLE 1

| | Cell viability assay | | | | | |
|---|---|---|---|---|---|---|
| Cell lines | 201T | H1975 | H3225 | A549 | Lung Fibroblasts | Bronchial Epithelial Cells |
| EGFR genotype | WT | Mutant (L858R/T790M) | Mutant (L858R) | WT | N/A | N/A |
| KRAS genotype | WT | WT | WT | G12S | N/A | N/A |
| CS3D $IC_{50}$ | 300 nM | 300 nM | 300 nM | 300 nM | 30 µM | 30 µM |

To assess the therapeutic potential of blocking STAT3 in NSCLC, a decoy approach was utilized by ligating a double-stranded 15-mer oligonucleotide that corresponds to the STAT3 response element within promoter regions of STAT3-target genes, to produce a cyclic STAT3 decoy (CS3D). The decoy was evaluated in vitro using NSCLC cells containing either wild-type (WT) EGFR (201T) or mutant EGFR with an additional EGFRi resistance mutation (H1975), as shown in FIG. 3A. These cells are resistant to EGFR inhibitors and require an alternate therapeutic approach. Initial studies showed that transfection of 0.3 μM of CS3D caused a 50% inhibition in proliferation in 201T (WT) and H1975 (mutant) cells, relative to CS3M, as well as a 2-fold increase in the percent of apoptotic cells. Toxicity was minimal in normal cells. Treatment with the active decoy CS3D led to potent anti-tumor effects, while the mutant construct CS3M was largely inactive.

To determine the concentration of CS3D required to inhibit cell viability, increasing concentrations of CS3D was transfected, and after 72 hours, MTS assays were used to assess cell viability. Data were normalized to cells treated with lipofectamine alone. The inactive mutant control (CS3M) showed no cytotoxicity (FIG. 3A), and the percent of cytotoxicity induced by CS3D allowed calculation of the $IC_{50}$s as described in Example 2. The $IC_{50}$ values for CS3D in both the WT (201T) and mutant (H1975) EGFR cell lines were approximately 0.3 μM (FIG. 3A). Other cell lines (H3225 with EGFR activating point L858R mutation and A549 which is EGFR WT) were also assessed in the presence of CS3D and CS3M and showed similar sensitivities ($IC_{50}$s 0.3 μM). Cell lines that are resistant to EGFR TKIs (201T, H1975, and A549) showed the same sensitivity to STAT3 decoy as the EGFR TKI sensitive cell line (H3225). Normal lung fibroblasts and primary bronchial epithelial cells had $IC_{50}$s that were 100-fold higher (300 μM) than tumor cells.

Uptake of CS3D into NSCLC Cell Lines

Figure 10:
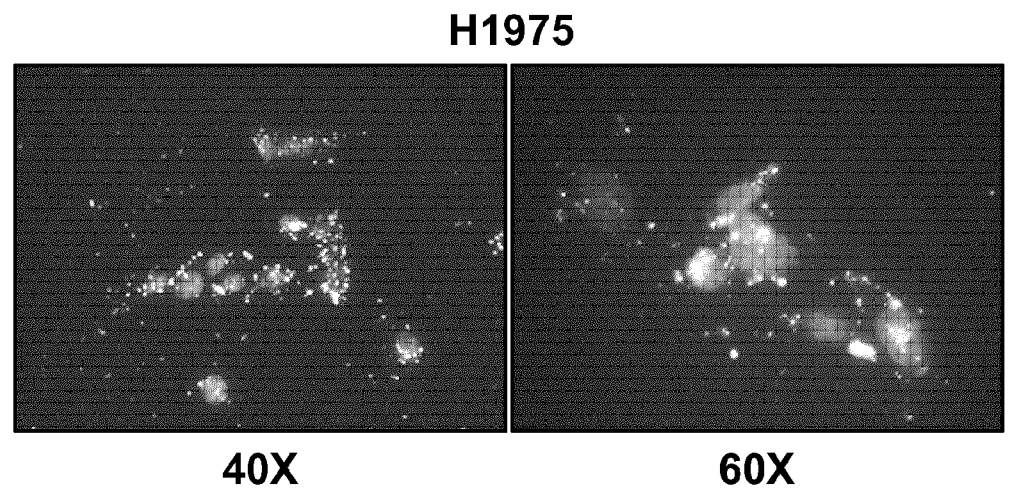
FIG. 10 shows localization of fluorecein-labelled CS3D by confocal imaging. H1975 cells transfected with 0.25 nM FITC labeled CS3D were fixed after 24 hr of transfection and imaged. confocal analysis revealed the presence of FITC labeled CS3D (green) within the Dapi stained nucleus (blue) and cytoplasm with a greater proportion detected in the cytoplasm. Images shown are 40× and 60× magnification.

To determine whether CS3D and CS3M were equally taken up by NSCLC cells, both molecules were tagged with a fluorescein dye (iFluorT) to assess transfection efficiency. Twenty-four hours post-transfection with the iFluorT-labeled oligonucleotides at a concentration of 25 nM. NSCLC cell lines showed intracellular location of the cyclic molecules (CS3D or CS3M), demonstrating that integrating hexaethyleneglycol linkers into the oligonucleotide, or circularizing the DNA, still allowed intracellular uptake. More importantly, altering the sequence of the CS3D by a single base-pair to generate the inactive STAT3 mutant (CS3M) did not affect its uptake, demonstrating that the cytotoxicity of CS3D was not due to preferential uptake compared to CS3M (FIG. 3B). The efficiency of transfection was >90% for both CS3M and CS3D. Further confocal microscopy showed clear fluorescent signal in both the nucleus and the cytoplasm of lung cancer cells, with cytoplasmic signal predominating. FIG. 10 shows localization of fluorecein-labelled CS3D by confocal imaging. H1975 cells transfected with 0.25 nnM FITC labeled CS3D were fixed after 24 hr of transfection and imaged. confocal analysis revealed the presence of FITC labeled CS3D (green) within the Dapi stained nucleus (blue) and cytoplasm with a greater proportion detected in the cytoplasm. Images shown are 40× and 60× magnification. This suggests that CS3D can interact with its target STAT3 dimers in both compartments.

CS3D Inhibits Colony-Forming Ability of NSCLC and Induces Cell Death

Figure 4A:
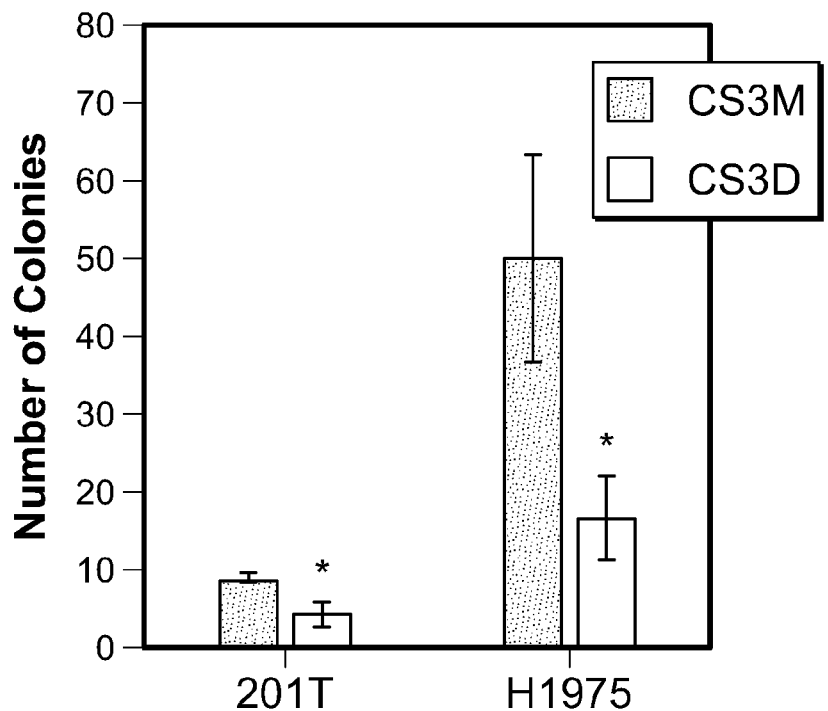
FIG. 4A shows CS3D inhibits anchorage independent growth. NSCLC cell growth was assessed in colony forming assays in the presence of either 300 nM CS3D or CS3M.

The effect of CS3D on the ability of NSCLC cells to grow in an anchorage-independent manner was examined. Cells (201T and H1975) were transfected with either CS3D or CS3M (300 nM), then seeded in soft agar. Compared with CS3M CS3D produced a significant decrease in colony formation. The number of colonies formed was quantified by using a size cutoff (with greater than 35 pixels counted as a colony). A single transfection with CS3D significantly (P<0.051) disrupted anchorage-independent growth of the NSCLC cells by 70% (at 15 days in H1975 cells) and 50% (at 20 days in 201T cells (P<0.053)) compared to CS3M. FIG. 4A shows CS3D inhibits anchorage independent growth and promotes apoptosis. NSCLC cell growth was assessed in colony forming assays in the presence of either 300 nM CS3D or CS3M. CS3D significantly blocks the ability of NSCLC to grow in an anchorage independent manner in soft-agar post-transfection. In a soft agar assay, one transfection reduced colony formation by 55% in 201T cells and by 65% in H1975 cells (P<0.05, FIG. 4A). One transfection also increased the number of apoptotic cells by 2-fold in all 4 cell lines and suppressed STAT3 target genes. Using one transfection of 300 nM CS3D or CS3M, followed by stimulation with 10 ng/ml EGF, expression of Myc and Bcl-xL (STAT3 response genes) was measured by RT-PCR. 1 hr after treatment with EGF. Expression of c-Myc and Bcl-Xl mRNA in response to EGF was reduced 60% or more by CS3D (P<0.05).

Figure 4B:
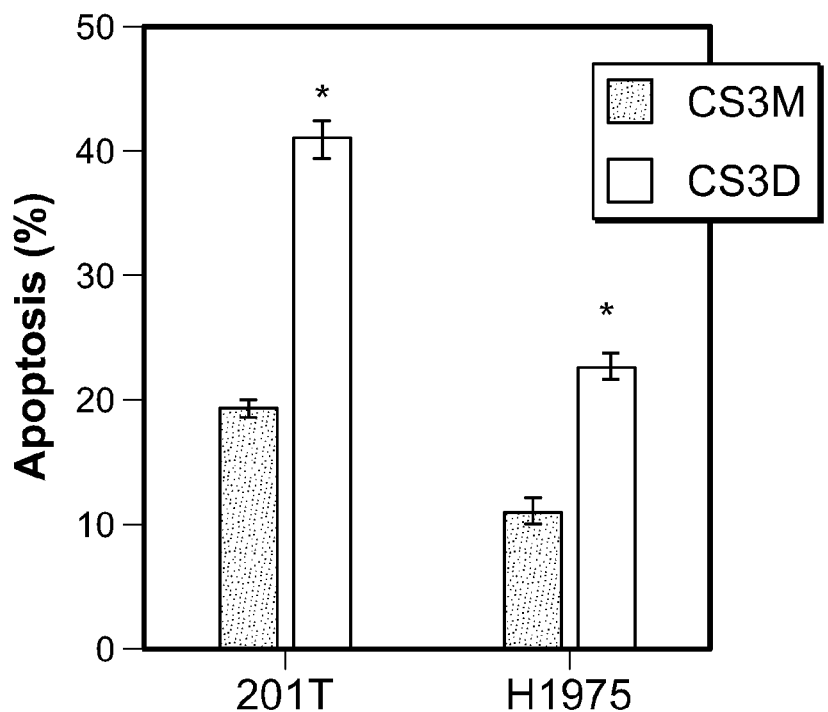
FIG. 4B shows detection of apoptosis by examining annexin V and propidium iodide (PI)-positive cells by flow cytometry: H1975 and 201T cells transfected with 100 nM of CS3M or CS3D for 24 hr were stained with apoptosis marker (annexin V) and cell viability dye. Statistical significance was determined as *P<0.05, n=3.

Flow cytometric analysis of Annexin V/propidium iodide-stained cells also demonstrated that transfection with CS3D significantly increased apoptosis in comparison to CS3M. CS3D treatment (100 nM) caused a 2-fold increase (P<0.05) in the number of cells undergoing apoptosis as compared to CS3M at 24 h. FIG. 4B shows detection of annexin V and propidium iodide (PI)-positive cells by flow cytometry: H1975 and 201T cells transfected with 100 nM of CS3M or CS3D for 24 hr were stained with apoptosis marker (annexin V) and cell viability dye. Statistical significance was determined as *P<0.05, n=3.

Figure 5A:
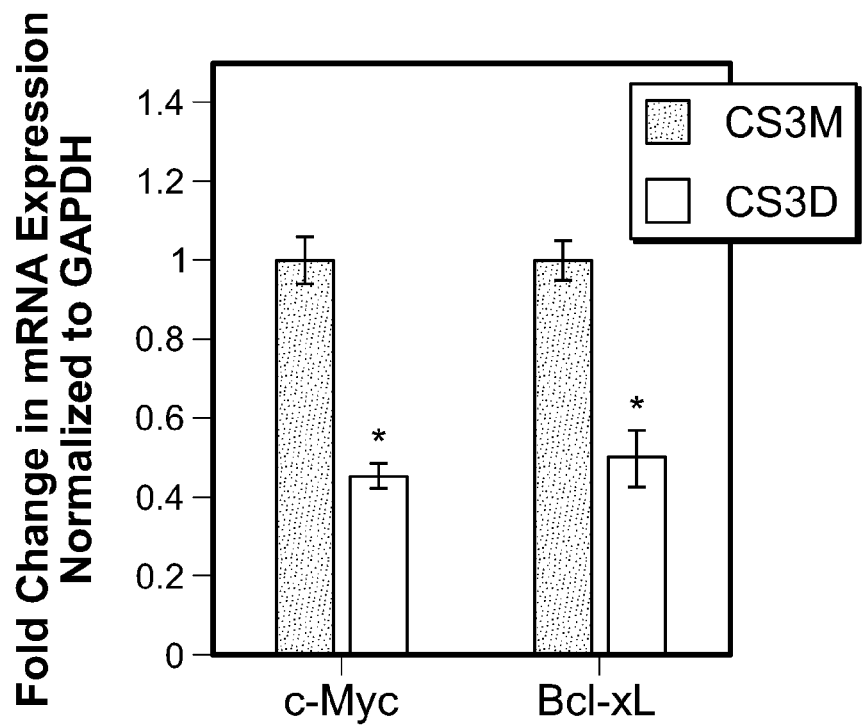
FIG. 5A shows down-regulation of c-Myc and bcl-xL mRNA expression by CS3D in NSCLC cells. Cells were treated 24 hours post-transfection with EGF (10 ng/ml) for 1.5 hr and mRNA was harvested from EGFR wild-type 201T cells. mRNA expression was assessed by RT-qPCR. Relative mRNA expression was normalized to GAPDH mRNA levels as an internal control. Statistical significance was determined as *P<0.05.
Figure 5B:
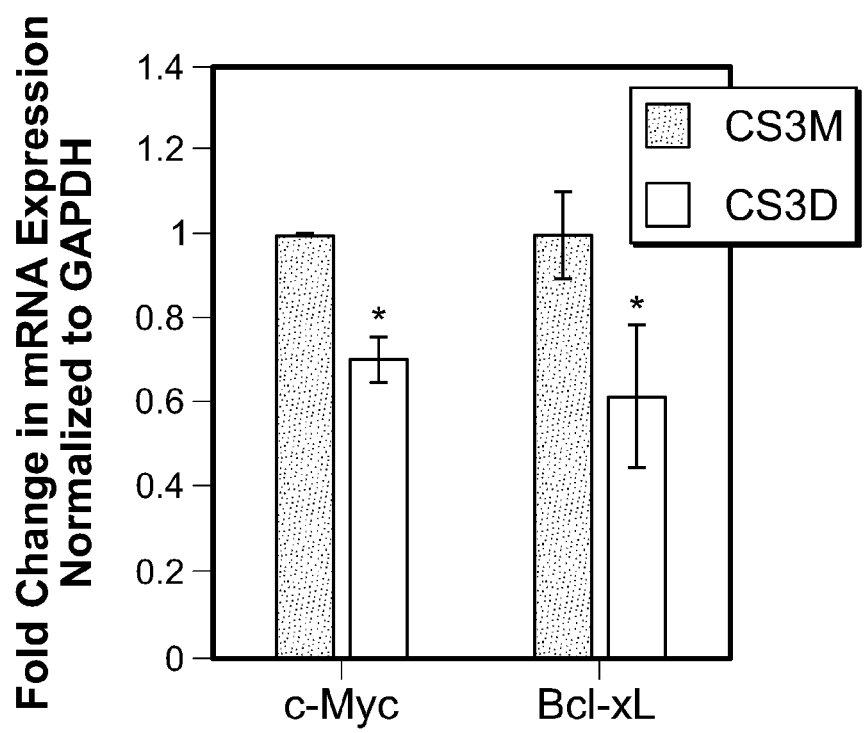
FIG. 5B shows down-regulation of c-Myc and bcl-xL mRNA expression by CS3D in NSCLC cells. Cells were treated 24 hours post-transfection with EGF (10 ng/ml) for 1.5 hr and mRNA was harvested from mutant EGFR T790M H1975 cells. mRNA expression was assessed by RT-qPCR. Relative mRNA expression was normalized to GAPDH mRNA levels as an internal control. Statistical significance was determined as *P<0.05.
Figure 6A:
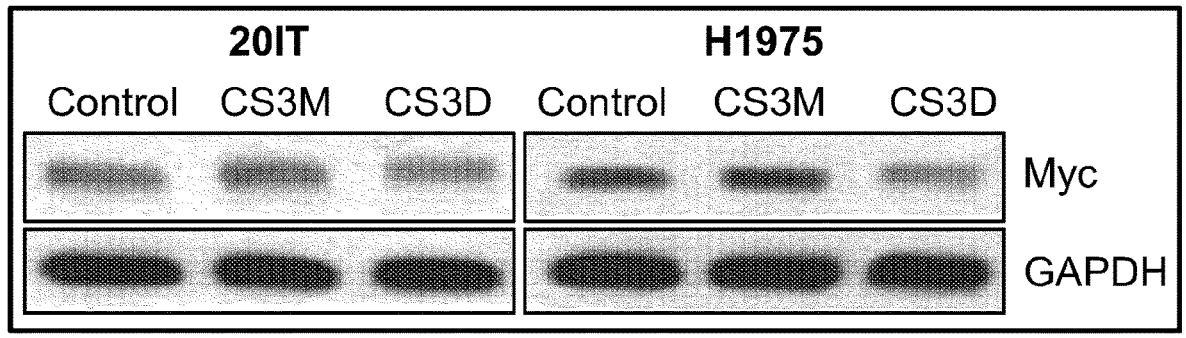
FIG. 6A shows down-regulation of c-Myc protein by CS3D. Cells were treated as in FIGS. 5A and 5B, and 3 hr after EGF treatment, lysates were collected from wild-type 201T (left) and mutant EGFR T797M H1975 (right) NSCLC cell lines.

CS3D Suppresses the Expression of c-Myc in Response to EGF c-Myc is a STAT3 target gene that is known to be activated by EGF treatment. To investigate the effects of STAT3 blockade on c-Myc expression, cells were first treated with 10 ng/ml EGF for 1.5 hr (deemed the optimal time to observe increased c-Myc RNA), 24 hr after transfection of the cyclic oligonucleotides. RT-qPCR was used to assess differences in mRNA expression in STAT3 decoy-treated versus mutant decoy-treated cells (FIGS. 5A and 5B). A single transfection of CS3D caused a 50% inhibition in mRNA level of c-Myc in 201T cells (FIG. 5A) and a 25-30% inhibition in H1975 cells (FIG. 5B). Immunoblotting analysis also showed a 31% reduction in c-Myc protein expression post-CS3D transfection compared to either CS3M or control (lipofectamine alone) in 201T cells. FIG. 5A shows down-regulation of c-Myc and bcl-xL mRNA expression by CS3D in 201T cells. Cells were treated 24 hours post-transfection with EGF (10 ng/ml) for 1.5 hr and mRNA was harvested from wild-type (A) and mutant EGFR T790M (B) NSCLC cell lines, and mRNA expression was assessed by RT-qPCR. Relative mRNA expression was normalized to GAPDH mRNA levels as an internal control. Statistical significance was determined as *P<0.05. FIG. 5B shows down-regulation of c-Myc and bcl-xL mRNA expression by CS3D in H1975 cells. Cells were treated 24 hours post-transfection with EGF (10 ng/ml) for 1.5 hr and mRNA was harvested from mutant EGFR T790M (B) NSCLC cell lines. Similarly, in H1975 cells, a 40% reduction in c-Myc protein expression was found. FIG. 6A shows down-regulation of c-Myc protein by CS3D. Cells were is treated as in FIGS. 5A and 5B, and 3 hr after EGF treatment, lysates were collected from wild-type 201T (left) and mutant EGFR T797M H1975 (right) NSCLC cell lines. Protein expression was assessed by Western blot. Relative c-Myc expression was normalized to GAPDH protein levels as an internal control. H3225 cells and A549 cells also showed similar decrease in c-Myc expression. Examination of other STAT3 genes (for example Bcl-xl as shown in FIGS. 5A and 5B) also responded with decreased mRNA and/or protein expression across the four cell lines, but not as consistently as c-Myc. Examination of STAT1 target genes (IKBKE, IFT2, IFT1, IRF7) and NFκB target genes (IL-IP and IL-8) that are predominantly regulated by these transcription factors showed no decrease in mRNA expression level by qRT-PCR when comparing CS3D to CS3M treated cells.

Figure 6B:
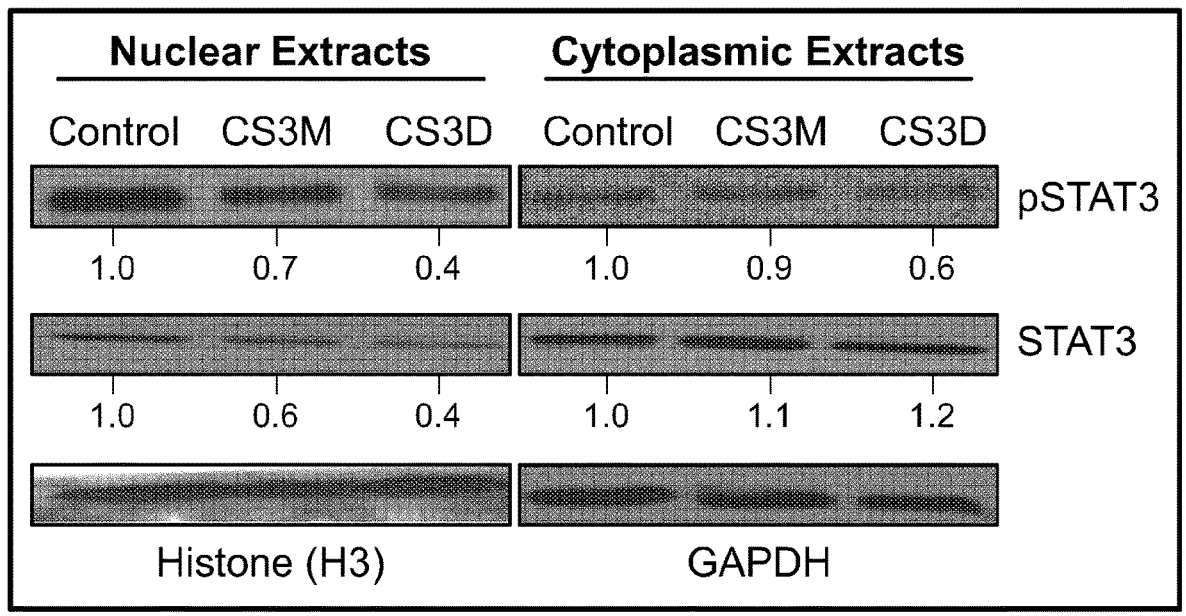
FIG. 6B shows CS3D degrades phospho-STAT3. H1975 were stimulated 24 hours post-transfection with either CS3M, CS3D, or lipofectamine alone with IL-6 (50 ng/mL) for 1 hr to strongly activate STAT3. After cell lysis, nuclear and cytoplasmic extracts were obtained by subcellular fractionation using centrifugation, and Western blotting was used to assessed to protein expression. GAPDH was used as a marker of the cytoplasmic fraction and histone H3 was used as a marker of the nuclear fraction. Densitometric quantification of the c-Myc bands are as indicated.
Figure 6C:
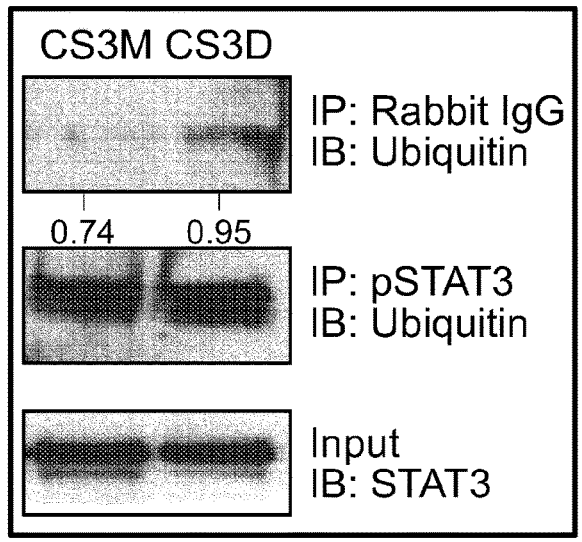
FIG. 6C shows evidence that CS3D causes the degradation of phospho-STAT3 through the ubiquitin-proteasome pathway. The proportion of pSTAT3-ubiquitin bound complexes was increased by CS3D compared to control CS3M. 24 hours post-transfection, P-STAT3 was immunoprecipitated and the presence of ubiquitin was assessed by immunoblotting, showing ability of CS3D to activate protein degradation of P-STAT3.

Additional immunoblotting analysis of cell extracts showed that after stimulation with IL6, a potent inducer of p-STAT3, there was a 35% reduction in both nuclear pSTAT3 and nuclear total STAT3 after transfection of CS3D compared to CS3M or control (lipofectamine alone) (FIG. 6B). The levels of pSTAT3 were reduced by CS3D, suggesting that the selective binding of pSTAT3 to CS3D alters its stability and causes it to degrade. H1975 were stimulated 24 hours post-transfection with either CS3M. CS3D, or lipofectamine alone with IL-6 (50 ng/mL) for 1 hr to strongly activate STAT3. After cell lysis, nuclear and cytoplasmic extracts were obtained by subcellular fractionation using centrifugation, and Western blotting was used to assessed to protein expression. GAPDH was used as a marker of the cytoplasmic fraction and histone H3 was used as a marker of the nuclear fraction. CS3D appears to have little effect on the cytoplasmic pool of total STAT3, but caused degradation of p-STAT3. In the nucleus, both the total STAT3 levels and the p-STAT3 levels were reduced showing that interaction with CS3D causes STAT3 to degrade. To test whether CS3D could increase ubiquitination of p-STAT3 protein, an immunoprecipitation was carried out for p-STAT3, followed by immunoblotting for ubiquitin. After 24 hr, CS3D increased the ratio of p-STAT3 that was ubiquitinated relative to amount of STAT3 present (input), compared to CS3M (0.95 vs. 0.74). FIG. 6C shows CS3D increases the proportion of pSTAT3-ubiquitin bound complexes. 24 hours post-transfection, P-STAT3 was immunoprecipitated and the presence of ubiquitin was assessed by immunoblotting. Greater ratio of pSTAT3-ubiquitin complexes was detected with CS3D treatment. The increase in pSTAT3-unbiquitin complex correlated with decrease in total STAT3 present. Densitometric analysis revealed a greater ratio of pSTAT3-ubiquitin complex to STAT3 in response to CS3D (0.95) as compared to CS3M (0.74). The input of total cell lysate also showed less STAT3 after CS3D treatment, confirming the results in FIG. 6B. This shows that CS3D increases the degradation of p-STAT3 by the ubiquitin proteasome pathway.

Figure 7A:
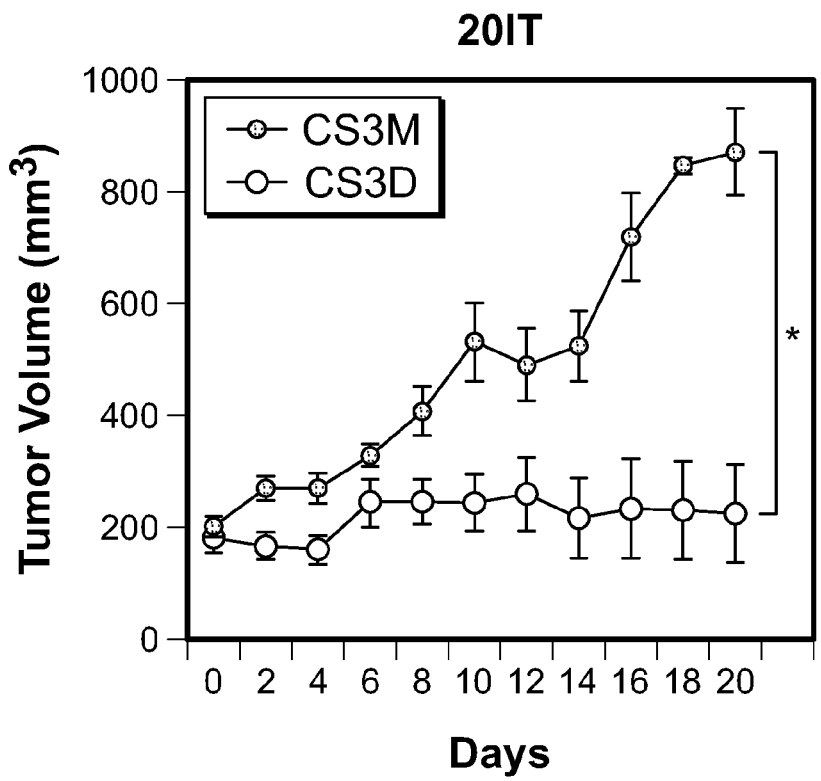
FIGS. 7A and 7B show CS3D suppresses NSCLC xenograft tumor growth. (A) Intravenous delivery of CS3D inhibits tumor growth in both (7A) wild-type (201T) and (7B) mutant EGFR T790M (H1975) xenografts. Approximately $1 \times 10^6$ cells were inoculated subcutaneously in the flanks of nude mice. Following the development of palpable tumors (about 200 mm), mice were randomized and given daily injections of either CS3D or CS3M (5 mg/kg/day; 10 tumors/group). Experiments were done twice as biological replicates. Tumor volumes were recorded every other day while animal weights were also monitored during the course of the treatment.
Figure 7B:
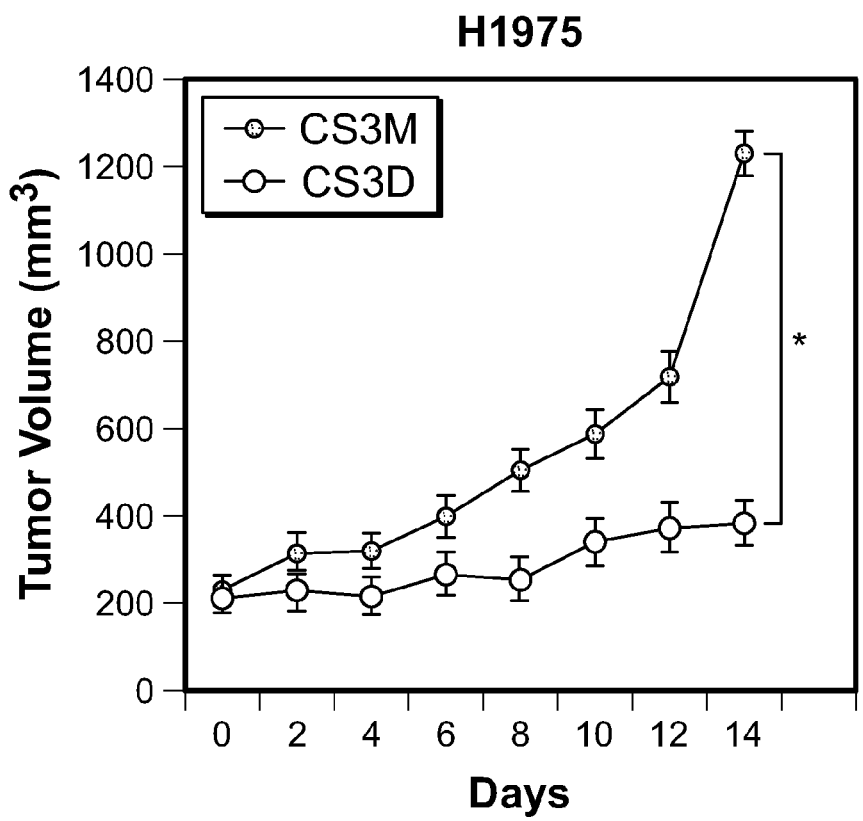

Intravenous Injection of the Cyclic STAT3 Decoy (CS3D) Inhibits NSCLC Tumor Growth In Vivo Based on the in vitro effects of CS3D, antitumor effects were evaluated in mice harboring established NSCLC xenografts (10 tumors/group). When tumors reached 200 mm3, mice were given daily intravenous injections (tail vein) of CS3D or CS3M (5 mg/kg/d), 5 days per week, and tumor growth was monitored for 14-20 days. CS3D caused a significant and robust tumor growth inhibition in 201T- and H1975-derived xenografts compared to treatment with CS3M. A 96.5% (P<0.007) was observed in 201T (FIG. 7A) and 81.7% (P<0.0001) reduction in H1975 (FIGS. 7A and 7B). Tumor growth at 14 days was inhibited over 85% by the active decoy in both KRAS WT cell lines (P<0.0001) as reported (Njatcha et al. *Proceedings of the American Association for Cancer Research* (2017) Volume 58; page 1048, Abstract #4101, April 2017. Available online Mar. 31, 2017).

FIGS. 7A and 7B show CS3D suppresses NSCLC xenograft tumor growth. Intravenous delivery of CS3D inhibits tumor growth in both wild-type (FIG. 7A, 201T) and mutant EGFR T790M (FIG. 7B, H1975) xenografts. Approximately $1 \times 10^6$ cells were inoculated subcutaneously in the flanks of nude mice. Following the development of palpable tumors (about 200 mm), mice were randomized and given daily injections of either CS3D or CS3M (5 mg/kg/day; 10 tumors/group). Experiments were done twice as biological replicates. Tumor volumes were recorded every other day while animal weights were also monitored during the course of the treatment. The difference in tumor volume between the CS3D- and CS3M-treated groups was significant for both 201T (P<0.007) and H1975 (P<0.0001).

Figure 7C:
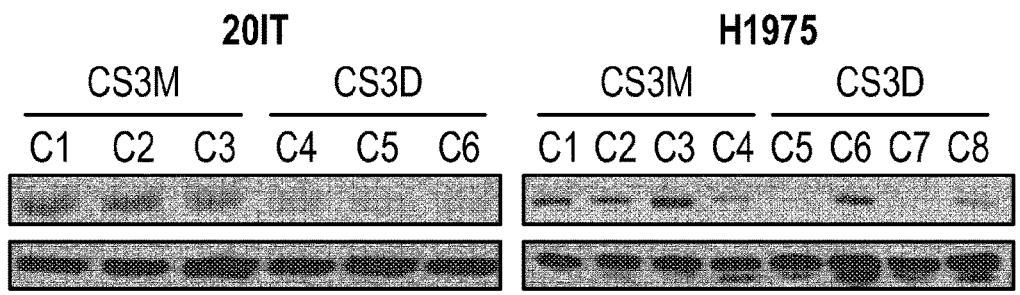
FIG. 7C shows c-Myc is suppressed after CS3D treatment in vivo. At the end of the treatments, tumors were harvested, whole cell lysates were prepared and RNA extracted for target gene analysis by Western blotting and RT-qPCR. GAPDH protein was used as internal loading control for immunoblotting. CS3D treated tumors (C4, C5, and C6) from separate animals show a decrease in c-Myc expression level relative to the CS3M-treated group (C1, C2, and C3) in 201T. Immunoblotting analysis of H1975 residual tumors treated with CS3D (C8-C8) also showed reduction in c-Myc expression levels relative to CS3M (C1-C4). The expression of c-Myc was significantly reduced in response to CS3D, relative to CS3M, in both wild-type (201T, (P<0.042)) and mutant EGFR (H1975, (P<0.05)) derived tumors (*P<0.05). Data are shown as mean+/−SEM.
Figure 7D:
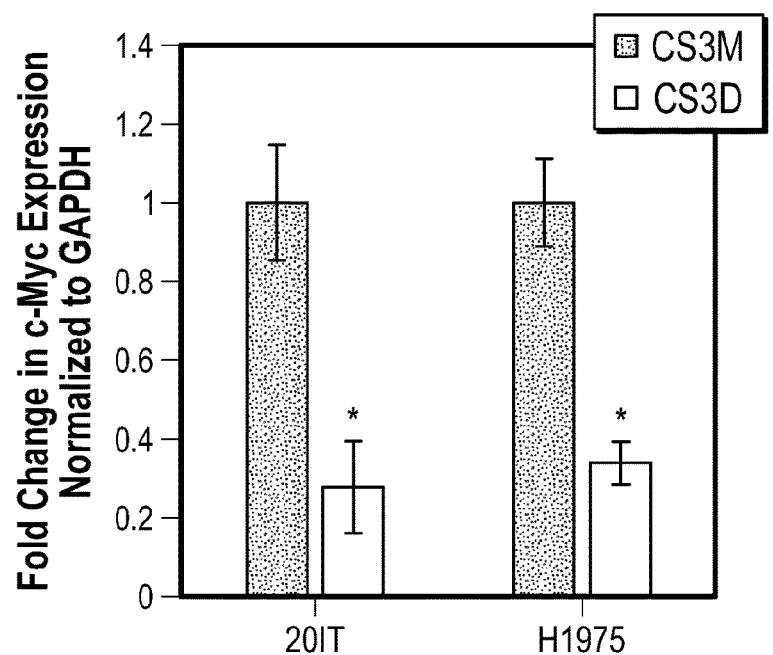
FIG. 7D shows densitometry quantification of c-Myc protein expression levels in 201T and H1975 from tumor-derived xenografts. The expression of c-Myc was significantly reduced in response to CS3D, relative to CS3M, in both wild-type (201T, (P<0.042)) and mutant EGFR (H1975, (P<0.05)) derived tumors. Data shown are means+/−SEM between two groups (CS3M and CS3D).

FIGS. 7C and 7D show c-Myc is suppressed after CS3D treatment in vivo. At the end of the treatments, tumors were harvested, whole cell lysates were prepared and RNA extracted for target gene analysis by Western blotting and RT-qPCR GAPDH protein was used as internal loading control for immunoblotting. CS3D treated tumors (C4, C5, and C6) from separate animals show a decrease in c-Myc expression level relative to the CS3M-treated group (C1, C2, and C3) in 201T. Immunoblotting analysis of H1975 residual tumors treated with CS3D (C8-C8) also showed reduction in c-Myc expression levels relative to CS3M (C1-C4). The expression of c-Myc was significantly reduced in response to CS3D, relative to CS3M, in both wild-type (201T, (P<0.042)) and mutant EGFR (H1975, (P<0.05)) derived tumors (*P<0.05). Data are shown as mean+/−SEM.

Figure 7E:
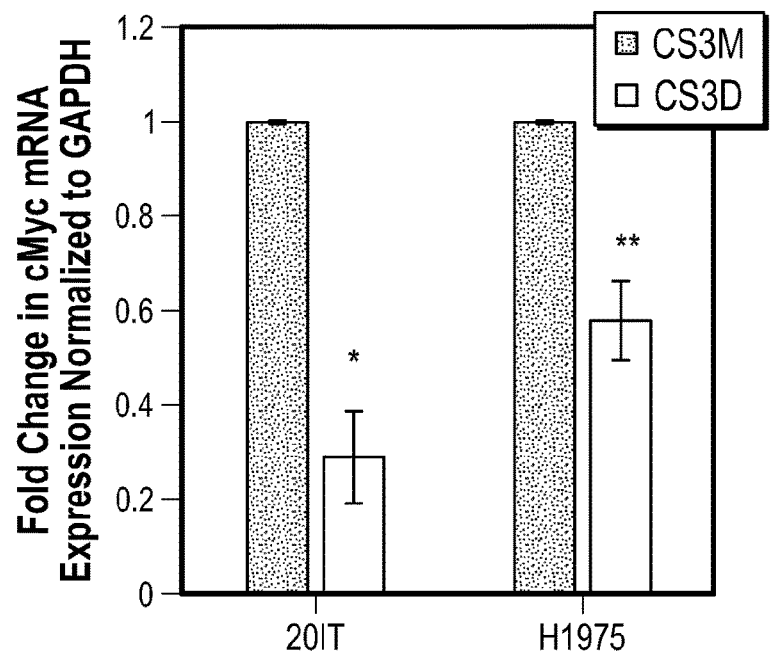
FIG. 7E shows c-Myc mRNA expression levels in 201T and H1975 tumor lysates. Data are presented as mean+/−SEM. *P<0.05 compared with the mutant control group (CS3M).

FIG. 7E shows CS3D suppresses c-Myc mRNA expression levels in 201T and H1975 xenografts (FIG. 7D). Data are presented as mean+/−SEM. *P<0.05 compared with the mutant control group (CS3M).

Figure 8A:
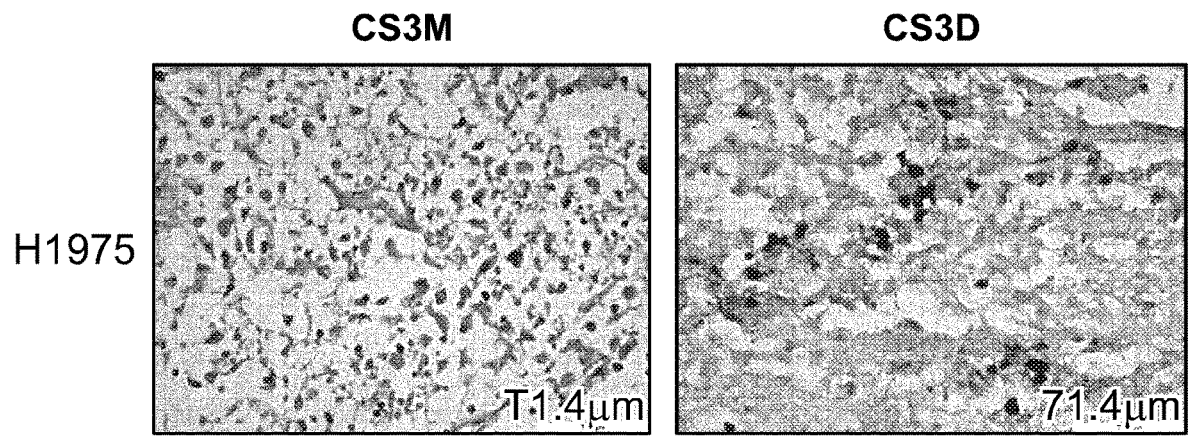
FIG. 8A shows STAT3 decoy induces caspase-3 cleavage. Representative sections of H1975 tumors stained for expression of cleaved caspase-3. H1975-derived xenografts administered daily intravenous injections of either CS3D or CS3M were harvested at the end of treatment (day 14), and expression of cleaved caspase-3 was used as a marker for apoptotic cells.
Figure 11:
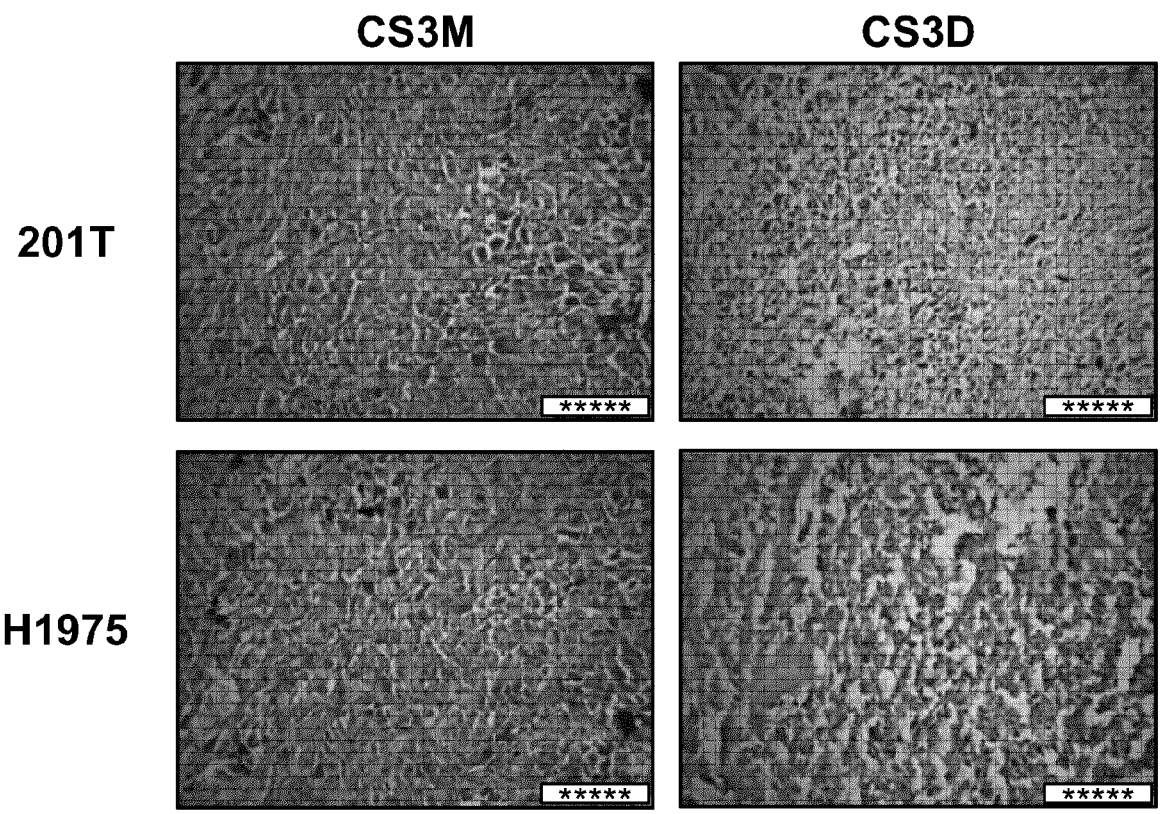
FIG. 11 shows long-term CS3D treatment alters tumor cellularity. H&E (hematoxylin and eosin) staining of 201T and H1975 harvested tumors following daily treatment with CS3D revealed a decrease in tumor cellularity and significant amount of debris as a result of apoptotic-mediated processes compared to CS3M that showed a more intact tissue architecture. Images were captured at 20× magnification.

Excised tumors showed grossly necrotic areas, as well as greatly increased caspase 3 staining. STAT3 target gene c-Myc protein was significantly reduced (P<0.01) in lysates from CS3D-treated tumors compared to CS3M (FIG. 8A). Staining (H&E, hematoxylin and eosin) of sectioned tumors harvested after treatment showed that the CS3D treated tumors were composed of large areas of debris and infiltration with stroma and lymphocytes, while the CS3M tumors had a high tumor cellularity. FIG. 11 shows long-term CS3D treatment alters tumor cellularity. H&E (hematoxylin and eosin) staining of 201T and H1975 harvested tumors following daily treatment with CS3D revealed a decrease in tumor cellularity and significant amount of debris as a result of apoptotic-mediated processes compared to CS3M that showed a more intact tissue architecture. Images were captured at 20x magnification. The animals showed no significant loss of body weight or decreased activity, and histological examination of the lungs, liver, and spleen showed no signs of toxicity with CS3D.

STAT3 Inhibition In Vivo by CS3D Down-Regulates c-Myc and Promotes Cell Death

To determine how CS3D blocks NSCLC growth, Western blot, qRT-PCR, and immunohistochemical analysis were performed to determine expression of c-Myc in residual tumors. These analyses identified a substantial downregulation of c-Myc protein (FIGS. 7C and 7D) and mRNA levels (FIG. 7E) in individual CS3D-treated tumors relative to CS3M-treated tumors in both 201T and H1975 xenografts. Some variability in protein levels among individual xenografts was observed (FIGS. 7C and 7D); the densitometry units for c-Myc protein after normalizing for GAPDH levels ranged from 0.11-0.16 units for CS3D-treated xenografts and 0.25-0.46 units for CS3M-treated tumors in H1975. Similarly, in 201T-derived tumors these measurements ranged from 0.015 to 0.51 units for CS3D and 0.28 to 0.97 units for CS3M. Even with this variability, the effect across the groups in both cell lines was significant ($P<0.05$ for H1975 and $P<0.042$ for 201T xenografts), with a mean decrease of 65% and 70%, respectively.

Figure 8B:
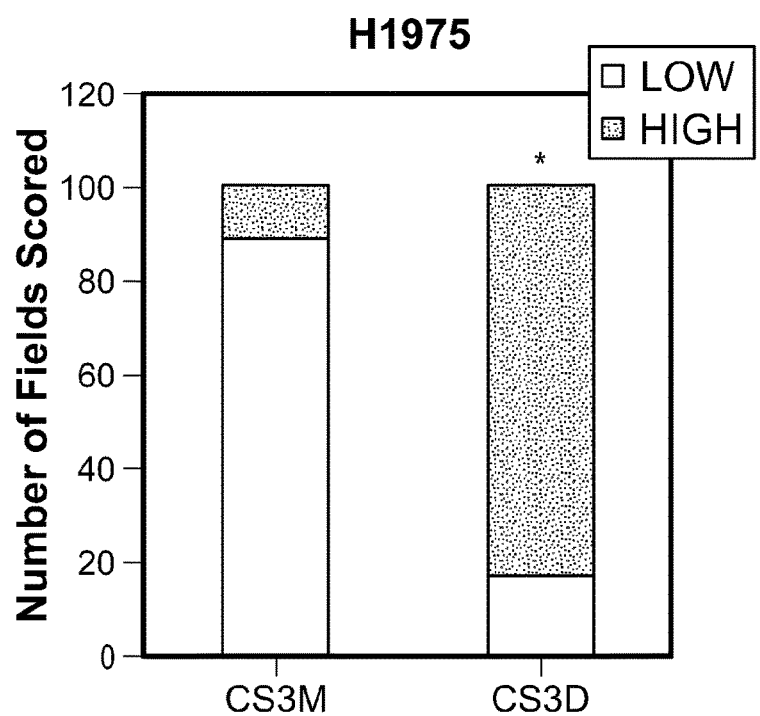
FIG. 8B shows a bar graph of STAT3 decoy induced caspase-3 cleavage from sections of H1975 tumors.

For mRNA levels in tumor lysates, CS3D produced a 60-70% reduction of c-Myc gene expression relative to GAPDH compared to CS3M (FIG. 7E). FIG. 8A shows immunohistochemical (IHC) analysis of tumors harvested after the last day of treatment also revealed a substantial increase in the levels of cleaved caspase-3 (observed predominantly in tumor cells) in response to CS3D. Sections of the H1975 xenografs in response to CS3M showed 10% of fields scoring for high level of cleaved caspase-3 whereas in CS3D-treated xenografs there was an increase to 83% of fields in the high scoring tumor sections ($P<0.05$). FIG. 8B shows a bar graph of STAT3 decoy induced caspase-3 cleavage from sections of H1975 tumors. Some cleaved caspase 3 staining was localized in nuclei, where caspase-3 is known to be active. Some caspase 3 staining was also evident in fibroblasts.

Figure 9A:
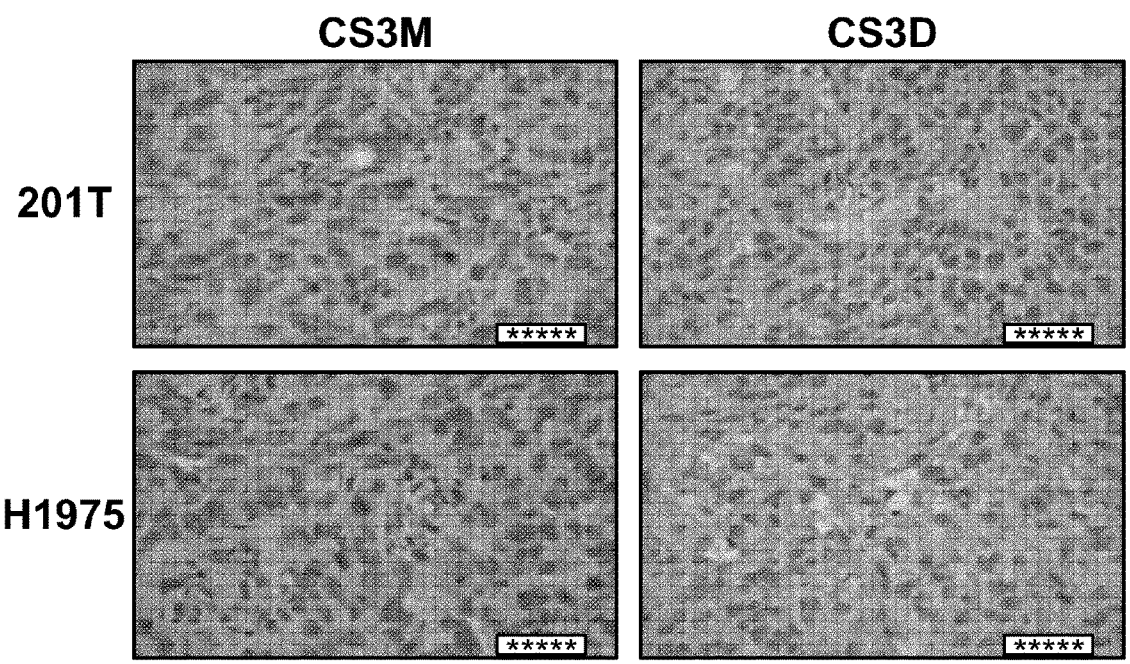
FIG. 9A shows short-term CS3D-treatment degrades p-STAT3. Level of p-STAT3 is reduced after five days of CS3D treatment compared to CS3M. Tumors derived from H1975 xenografts were analyzed by immunohistochemical staining for p-STAT3 after 5 daily iv injections of either STAT3 decoy or mutant decoy.

Short-Term CS3D Treatment Shows Anti-Tumor Effects Including Degradation of Nuclear p-STAT3 In Vivo Because tumors treated for several weeks with the STAT3 decoy were largely composed of debris (as illustrated in FIG. 11), xenografts were examined after only 5 daily tail vein injections to determine what cellular changes were induced prior to collapse of the intracellular tumor structure. FIG. 9A shows short-term CS3D-treatment suppresses p-STAT3 protein levels in the xenografts. Tumors derived from H1975 xenografs were analyzed by immunohistochemical staining for p-STAT3 after 5 daily iv injections of either STAT3 decoy or mutant decoy. Representative sections of H1975 tumors show a decrease in p-STAT3 protein levels consistant with a degradation of STAT3 in vivo in the xenografts, as was observed in vitro in cells in FIGS. 6B and 6C. This effect is quantified in FIG. 9B.

FIG. 10 shows confocal imaging of iFluor-labeled C53D showing the STAT3 decoy/degrader is localized in the nucleus and found in the cytoplasm within structures that appear to be endosomes.

Figure 9B:
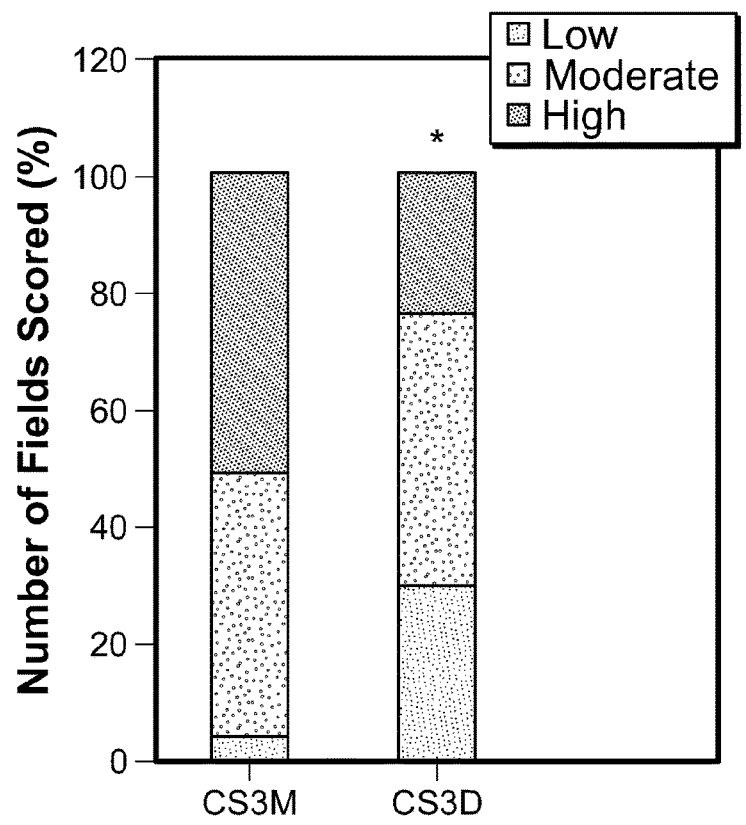
FIG. 9B shows bar graph quantitation of the frequency of low-, medium-, and high-grade p-STAT3 staining in multiple images; P<0.001, decoy compared to mutant quantifying the degration of p-STAT3. Bright field images were captured at 40× magnification.
Figure 12A:
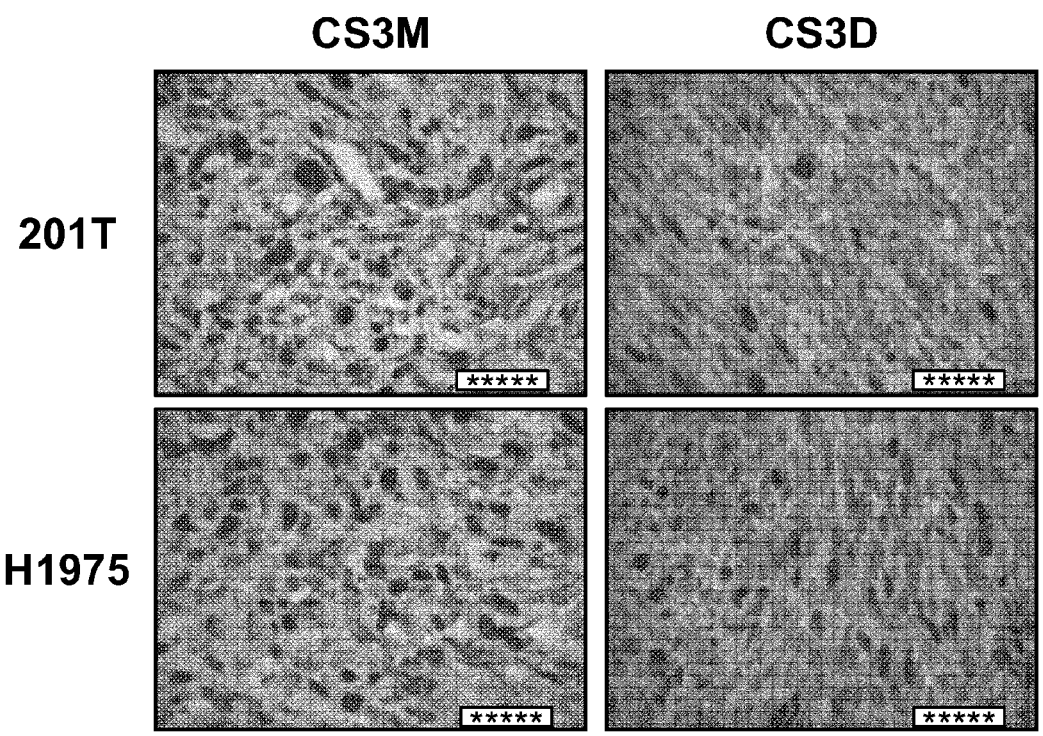
FIG. 12A shows short-term CS3D-treatment decreases Ki-67 expression. Immunohistochemical analysis using a Ki-67 monoclonal antibody revealed a decrease in the proportion of Ki-67 positive cells in CS3D-treated tumors after five days, compared to CS3M.
Figure 12B:
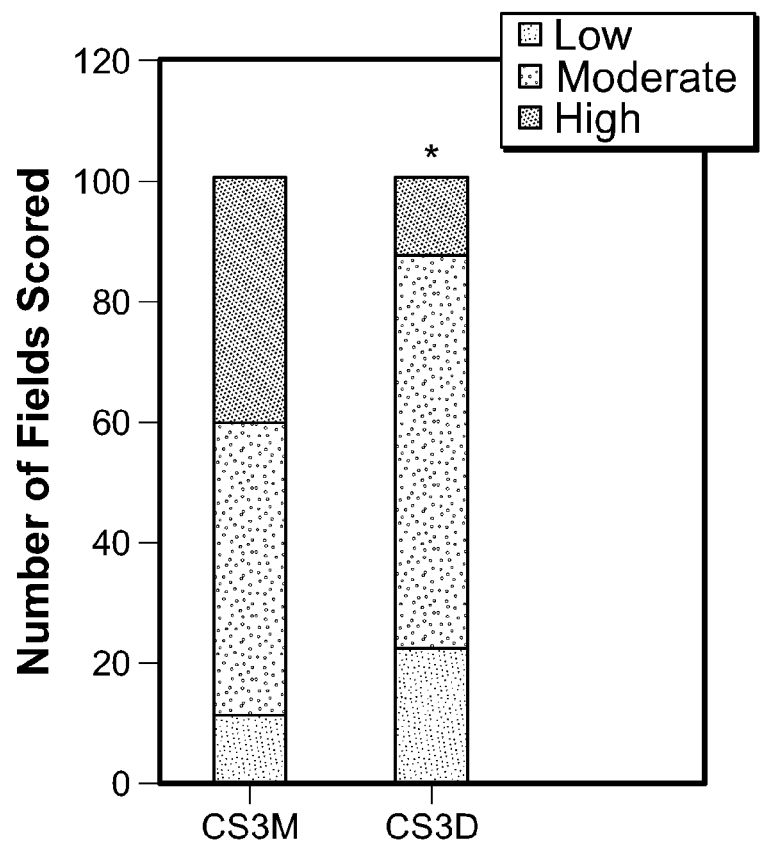
FIG. 12B shows a bar graph of frequency of low-, medium-, and high-grade Ki-67 staining in multiple images; P<0.001, decoy compared to mutant. Images were captured at 40× magnification.

FIG. 11 shows histological changes (H&E staining) were consistent with disaggregation of malignant cells in CS3D-treated tumors. Further analysis by immunohistochemical (IHC) staining revealed a significant decrease in the proliferative capacity of NSCLC, shown by Ki-67 staining in response to CS3D-treatment (*$P<0.001$) compared to CS3M-treated tumors after 5 daily injections. FIG. 12A shows short-term CS3D-treatment decreases Ki-67 expression. Immunohistochemical analysis using a Ki-67 monoclonal antibody revealed a decrease in the proportion of Ki-67 positive cells in CS3D-treated tumors after five days, compared to CS3M. FIG. 12B shows a bar graph of frequency of low-, medium-, and high-grade staining in multiple images; $P<0.001$, decoy compared to mutant. Images were captured at 40× magnification. A shift from 41% of cells was observed and scored as high-grade staining with CS3M treatment to 13% with high-grade staining in the presence of CS3D, with corresponding increases in moderate- and low-grade staining in the STAT3 decoy treated group (FIG. 12B). Expression levels of p-STAT3 protein (which was mainly observed localized to the nucleus) were likewise significantly suppressed by the STAT3 decoy (*$P<0.0001$) after 5 days of treatment in vivo compared to mutant decoy. FIG. 9B shows bar graph quantitation of the frequency of low-, medium-, and high-grade staining in multiple images; $P<0.001$, decoy compared to mutant. Bright field images were captured at 40× magnification. Frequency of high-grade staining for p-STAT3 differed between CS3D and CS3M treatment groups (23% in CS3D-treated and 51% in CS3M treated, with corresponding increase in low-grade staining in presence of the active decoy (FIG. 9B). Significant degradation of p-STAT3 protein was detected by IHC in tumors was observed after treatment with CS3D. Percent of high staining fields was reduced from 48% to 22% while percent of fields with low staining increased, $P<0.001$ (FIG. 9B).

The p-STAT3 result suggests that multiple doses of the decoy promoted the degradation in p-STAT3 levels in vivo. At this early time point, no induction of apoptosis was observed (not shown), suggesting that effects on STAT3 and proliferation occur prior to an increase in cell death. No change in NF-κB nuclear protein was observed with the active decoy after five days of treatment, suggesting that the decoy does not induce NK-κB movement to the nucleus.

The strong activity of CS3D in vivo on reducing p-STAT3 and c-Myc levels, and reducing tumor growth, may reflect greater effect upon repeated in vivo dosing, compared to the single exposure by transfection used in vitro. No differences in weight, food intake or motor activity with CS3D, and no histologic changes in spleen, liver, or lungs were observed.

Figure 13A:
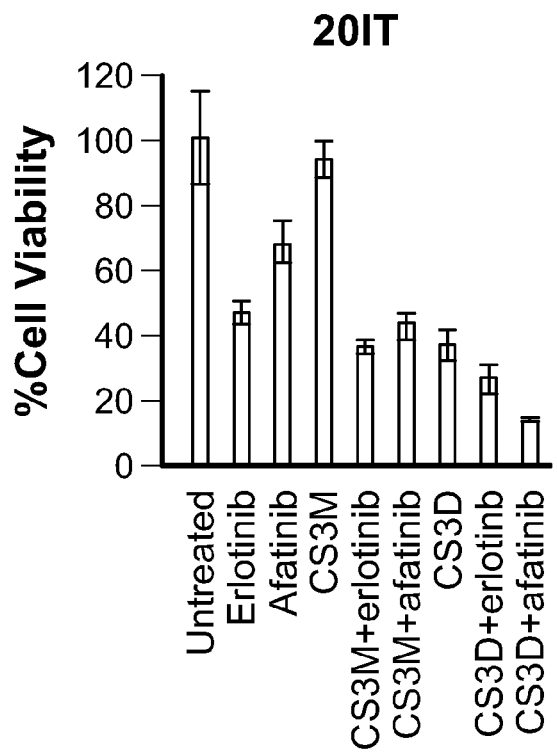
FIG. 13A shows combination treatment results by 201T cell viability assessed at 48 hr by MTS assay. Results from triplicate wells in 96 well plates.
Figure 13B:
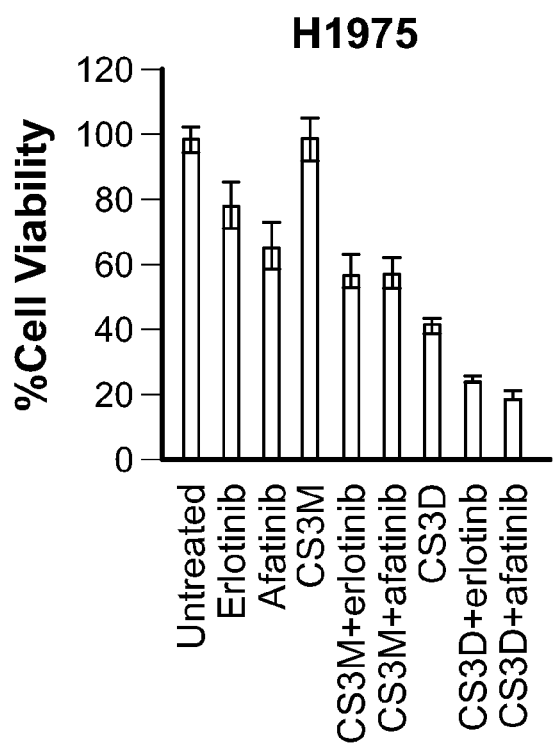
FIG. 13B shows combination treatment results by H1975 cell viability assessed at 48 hr by MTS assay. Results from triplicate wells in 96 well plates.

The combination of CS3D with EGFR TKIs showed enhanced effects in both EGFR WT and EGFR mutant/erlotinib resistant NSCLC (FIGS. 13A and 13B). FIG. 13A shows combination treatment results by 201T cell viability assessed at 48 hr by MTS assay. Results from triplicate wells in 96 well plates. FIG. 13B shows combination treatment results by H1975 cell viability assessed at 48 hr by MTS assay. Results from triplicate wells in 96 well plates. The effect of the afatinib (GILOTRIF®, Boehringer Ingelheim) 5 μM (micromolar)/CS3D 300 nM combination gave the best inhibition compared to other single or double treatments in cell culture. Afatinib (GILOTRIF®, Boehringer Ingelheim) is an irreversible inhibitor of EGFR/HER2/HER4 with superior clinical activity to erlotinib in NSCLC. This effect was synergistic ($P<0.05$) when multiple concentrations were tested, yielding a combination index of 0.4.

CS3D is a novel therapeutic that targets STAT3, a cyclic, double-stranded decoy oligonucleotide with the surprising and unexpected properties of a long half-life, high potency, and limited toxicity and ability to induce degradation of STAT3. The CS3D STAT3 oligonucleotide decoy specifically and competitively binds activated STAT3 protein via its similarity to the STAT3 response element located in the promoter region of the c-fos gene, and to reduce expression of STAT3 target genes in head and neck cancer models. Head and neck cancer cells also responded to the CS3D STAT3 decoy in a xenograft model.

The CS3D STAT3 decoy produces a robust antitumor effect in NSCLC models that are known to be resistant to FDA-approved EGFRi therapies. In cell culture, CS3D decreased the viability of NSCLC cells and induced apoptosis, and sensitivity was independent of EGFR mutation status. These effects were specific compared to a mutant version of the mutant CS3M double-stranded decoy that is unable to recognize STAT3 protein and were demonstrable after a single transfection. Further in vivo studies illustrated that daily IV injection of the active decoy had strong anti-tumor effects in mouse xenograft models of NSCLC, accompanied by inhibition of c-Myc protein expression and destruction of the cellular integrity of tumor cells within the xenografts. When tumors were analyzed after only 5 daily treatments, nuclear p-STAT3 protein was greatly reduced consistent with degradation by the proteasome and the proliferative state of tumor cells was also greatly decreased. Since the phosphorylation step that activates STAT3 is not affected by CS3D STAT3 decoy, this result suggests one effect of the decoy is to reduce accumulation of p-STAT3 in the nucleus. This finding was consistent with the observed decrease in the nuclear pool of STAT3 and increase in ubiquitination of p-STAT3 protein following CS3D treatment in vitro. The cytoplasmic pool of p-STAT3 was also reduced by CS3D treatment in vitro, which could result from increased degradation of STAT3 dimers when bound to the active decoy. A CS3D-pSTAT3 dimer complex may trigger a ubiquitination process that reduces the amount of active STAT3 available for signaling in the nucleus.

STAT3 is primarily activated by modification through phosphorylation at tyrosine and serine residues (Y705 and S727) that effectively initiates dimerization of STAT3 monomers. However, small molecule inhibitors of STAT3 that inhibit phosphorylation, might be ineffective in blocking the functional activity of STAT3 dimers that do not require phosphorylation to initiate dimerization. This strategy also requires a very efficient inhibition of the phosphorylation step, which might limit efficacy. The use of CS3D as a STAT3 decoy inhibitor provides an opportunity to interrupt the functional activity of STAT3 dimers, without requiring the interruption of phosphorylation. Potentially this strategy could be more effective, because it focuses on the active dimeric moieties. CS3D specifically downregulates the expression of the STAT3 target gene c-Myc in NSCLC cell lines in culture and in residual tumors after systemic administration. The transcriptional activity of STAT3 overlaps with other transcription factors such as STAT1 and NF-κB, but genes controlled predominantly by STAT1 or NF-κB such as IRF7 and IL-8 were unaffected by CS3D treatment. Although c-Myc is a direct STAT3 target gene, it is possible that indirect effects on c-Myc mRNA or protein expression could also be occurring in response to the STAT3 decoy.

The cyclic double-stranded oligonucleotide showed enhanced stability compared to linear versions (Sen et al, *Cancer Discovery* (2012) 2:694-705) and was efficacious after iv injection in a head and neck cancer model. In addition to relative lack of toxicity seen with the STAT3 decoy against normal lung cells and in mice used for xenograft studies, the decoy effects were also specific since the mutant inactive control oligonucleotide (which differs by a single base-pair mutation) was unable to induce anti-tumor effects. The cellular uptake of fluorescently labeled CS3D and CS3M also did not differ, supporting the specificity of the decoy that is designed to bind with selectivity to dimeric STAT3 protein. Imaging analysis also showed that the localization of CS3D mostly stained positively in the cytoplasm, although some was present in the nucleus, suggesting the main effect is to bind to pSTAT3 dimers in the cytoplasm. The uptake and anti-tumor effects of CS3D were comparable in both EGFR wild-type and mutant NSCLC. It has been reported that the constitutively active mutant form of STAT3, STAT3-C, which is dimerized by cysteine-cysteine residues, mediates epithelial cell transformation by promoting anchorage-independent growth (Bromberg J F, et al. *Cell* (1999) 99:238-239), suggesting that this phenotype is especially dependent on STAT3 signaling. After a single transfection, CS3D was very effective in suppressing anchorage-independent growth. The inhibition of c-Myc expression in cultured cells and in xenografts also was a strong indicator of CS3D activity, suggesting that the ability to suppress this STAT3 target gene may be critical for its anti-tumor mechanism in NSCLC. The c-Myc protein binds to promoter regions of genes encoding lung cancer stem cell factors such as SOX2 and nanog, and cooperates with STAT3 in regulating these genes (Kidder B L, et al *PLOS ONE* (2008) 3(12): e3932. doi:10.1371/journal.pone.0003932), further suggesting that c-Myc down-regulation caused by reduction in STAT3 action may be important in the anti-tumor action of CS3D in NSCLC, especially in reducing stem cell self-renewal.

The cyclic decoy oligonucleotide-based approach exhibited strong therapeutic activity in NSCLC, an effect that was also observed in HNSCC. The non-cyclic version of the STAT3 decoy injected intratumorally into HNSCC patients in a Phase 0 trial produced remarkable effects by altering the expression of STAT3 target genes critical for the progression of HNSCC. The results support the ability of a systemically administered, double-stranded, cyclic oligonucleotide decoy to attenuate STAT3 signaling in a lung cancer model, which ultimately leads to tumor growth arrest and cell death. No increase in nuclear NF-κB protein in lung tumor xenografts was observed after decoy treatment, suggesting that the STAT3 decoy does not increase NF-κB nuclear translocation, as has been reported in a STAT3 knockout KRAS lung cancer model (Grabner B. et al, *Nature Communications* (2015) 6:6285). The observed effects in NSCLC support the idea that a circularized double-stranded oligonucleotide targeting STAT3 has promise as a therapeutic agent and may be effective in lung tumors that lack sensitivity to EGFR TKIs. The cyclic STAT3 decoy lacks toxicity in immunocompetent mice, and no toxic effects were observed in the immunosuppressed animals used here.

Methods of Chemoprevention

Methods of the invention include the chemoprevention of cancer by administering to a patient in need or at risk a therapeutically-effective dose of a STAT3 Blocker/Degrader. The STAT3 Blocker/Degrader modulates one or more targets selected from STAT3 mRNA, STAT3 monomer, phosphorylated STAT3, acetylated STAT3, activated STAT3, STAT3 homodimer, and STAT3-STAT1 heterodimer. Methods of the invention include the chemoprevention of non-small cell lung cancer by administering a therapeutically-effective dose of a STAT3 Blocker is administered to the patient.

A patient to be treated with a STAT3 Blocker/Degrader according to the methods of the invention may be at elevated risk of developing cancer, due to one or more factors selected from a genetic condition, immunocompromised status, comorbidities, prior treatment for cancer, incidence of cancer, prior treatment with or exposure to one or more chemotherapeutic agents, radiation therapy, exposure to radiation or radon, prior exposure to or treatment with one or more carcinogenic or cytotoxic agents, and social or family history correlated with the incidence of cancer. The factors include, but are not limited to, exposure to asbestos and smoking.

In one embodiment, the STAT3 Blocker/Degrader is given for the purposes of chemoprevention to patients who do not meet clinical guidelines for diagnosis of cancer. In another embodiment, the STAT3 Blocker is given for the purposes of chemoprevention to patients who have evidence of preneoplastic or dysplastic cells, but do not meet the guidelines for clinical diagnosis of cancer. In another embodiment, the STAT3 Blocker is given to patients currently in remission from a prior diagnosis of cancer. In another embodiment, the STAT3 Blocker is given to patients who had a complete resection of a cancer and who have no current evidence of disease.

Any method of delivery of the STAT3 Blocker/Degrader to patients can be used including, without limitation, inhalation (including, without limitation, metered dose inhalation, dry powder inhalation, inhalation of aqueous suspension, inhalation of lipophilic suspension, inhalation of emulsion, inhalation of organic-based suspension), IV, topical, locally delivered during invasive procedure, transdermal, subcutaneous injection, intramuscular injection, sublingual, suppository, eye drops, ear drops, PO, injection, infusion, continuous infusion, or depo injection. As used herein, a patient may be a human or animal of any kind, including, without limitation, a mammal, non-human primate, canine, or feline.

CS3D is Active in Chemoprevention of Lung Cancer without Causing Toxicity

In a pilot experiment, 6 FVB/N mice were given 24 mg NNK (3 mg by ip injection, twice a wk×4 wks), followed by 6 wks rest, then IV treatment of 3 mice with either 5 mg/kg CS3D or CS3M 5 days a wk for 18 wks. A considerable reduction in tumor burden was found with CS3D, and CS3D showed no discernable toxic effects, while mice receiving CS3M lost weight and had breathing difficulties. With CS3M, lungs were filled with multiple invasive adenocarcinomas, while in mice receiving CS3D, tumor burden was reduced over 80%. H&E (hematoxylin and eosin) sections were taken of murine lungs exposed to NNK followed by treatment with CS3M or CS3D for 18 wks. Invasive carcinomas were prominent with CS3M and lacking with CS3D.

Figure 14A:
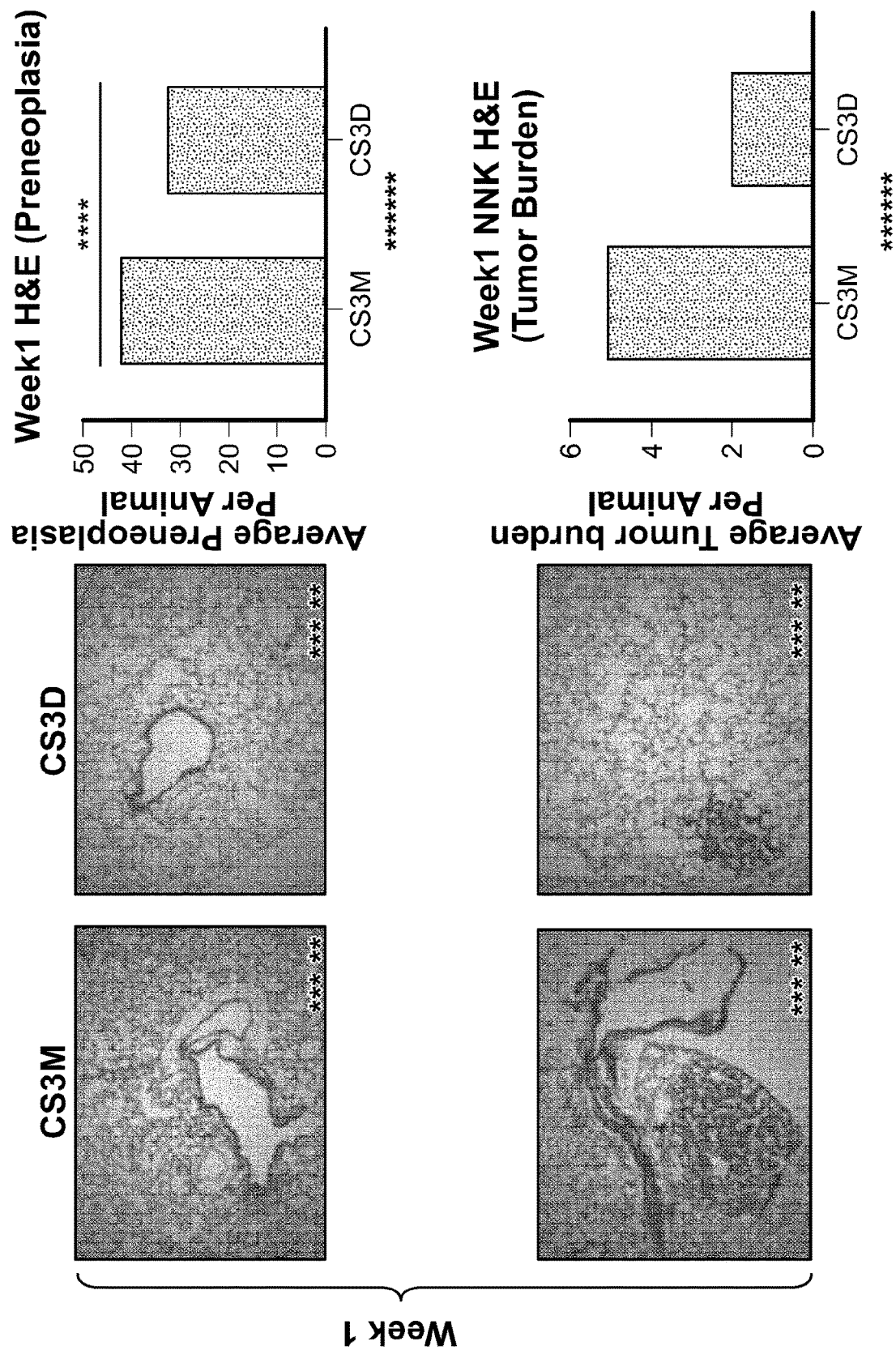
FIG. 14A shows a chemopreventive effect of CS3D by examining histology of preneoplasias and lung tumors, and bar graphs of counts of preneoplasias and tumors, in the lungs of mice that had previously received the carcinogen NNK. Lungs were examined 1 week after the 8 week treatment with CS3M or CS3D ended, showing a chemopreventive effect. Preneoplasias were reduced by CS3D (P<0.001) after 1 week. Tumor burden per animal was also reduced.

To confirm these findings, in a second experiment, in which 24 mg NNK was given (3 mg by ip injection, twice a wk, ×4 wks,), this was followed by one week rest and then immediate treatment with 5 mg/kg CS3D or CS3M, 3 daily injections per week, for 8 weeks. Then 1 week, 8 weeks, or 20 weeks after the end of the treatment course (13 weeks, 21, and 33 weeks after beginning the NNK exposure), necropsy was performed. Mice treated with CS3D were compared to CS3M-treated control group and no body weight changes were observed or organ toxicity (by histological analysis of the liver and spleen) was detectable. Lung tumors were evaluated by inspecting formalin-fixed lungs visually and by histology after H & E staining. Histopathological analysis of the lungs from CS3D treated mice revealed approximately 25% fewer number of preneoplasias on average per animal (detected as thickened epithelial cell layer in the airways) as compared to CS3M at week 1 post-CS3D administration (FIG. 14A). Tumor burden (detected by neoplastic growths [adenomas] observed in lung sections) was also assessed at the week 1 timepoint after treatment. Consistent with reduction in preneoplasia, we observed a decrease in the average number of tumors (a 60% reduction in tumors in the CS3D-treated animal) (FIG. 14A).

Figure 14B:
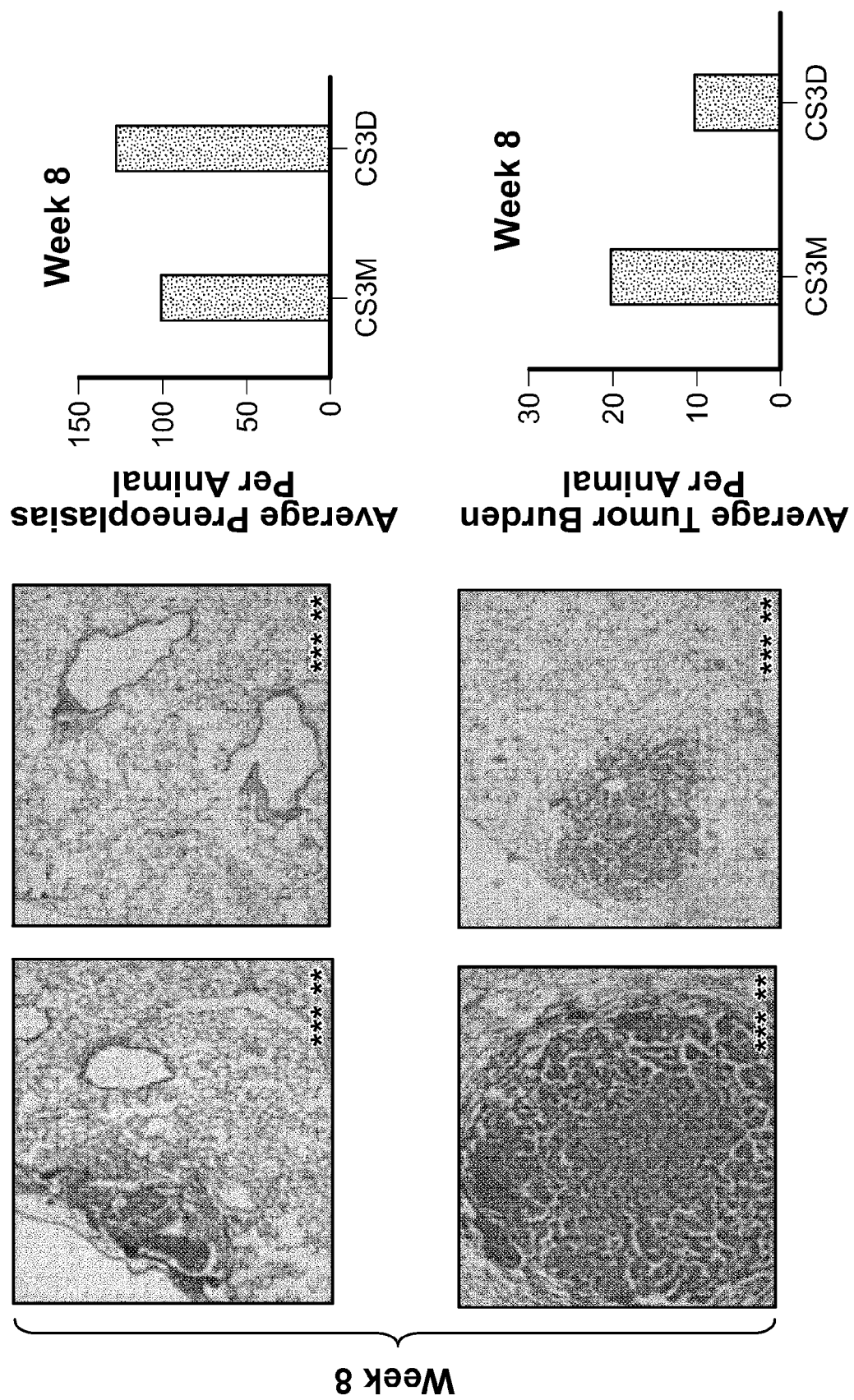
FIG. 14B shows histology of preneoplasias and lung tumors, and bar graphs of counts of preneoplasias and tumors in mice exposed to NNK, 8 weeks after the 8 week treatment ended, showing a chemopreventive effect. Tumors were reduced 8 weeks after treatment ended by CS3D, while the number of preneoplasias were increased, compared to CS3M, showing that preneoplasias were inhibited in progression to tumors.

To determine if the effects of CS3D is sustainable in a long-term experimental model, sections from lung tissue harvested at the 8 weeks post-treatment were examined and a 52% lower number of adenomas from the CS3D group compared to the CS3M control group was found (FIG. 14B). But in contrast, the CS3D-treated group showed a 43% higher count of preneoplasia compared to CS3M 8 weeks after treatment ended, showing an inhibition of tumor transition from prenoplasia to adenoma by CS3D.

Figure 15A:
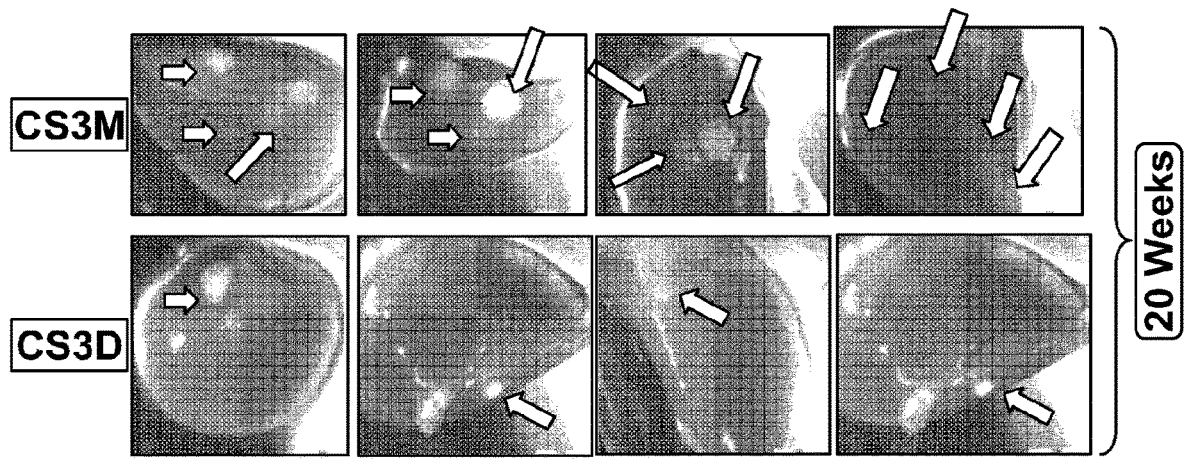
FIG. 15A shows photographs of lungs taken from NNK-exposed mice treated with either inactive CS3M control or active CS3D, 20 weeks after the end of the 8-week drug treatment (6.5 months after NNK exposure), showing a chemopreventive effect with fewer visible tumors in CS3D treated animals.
Figure 15B:
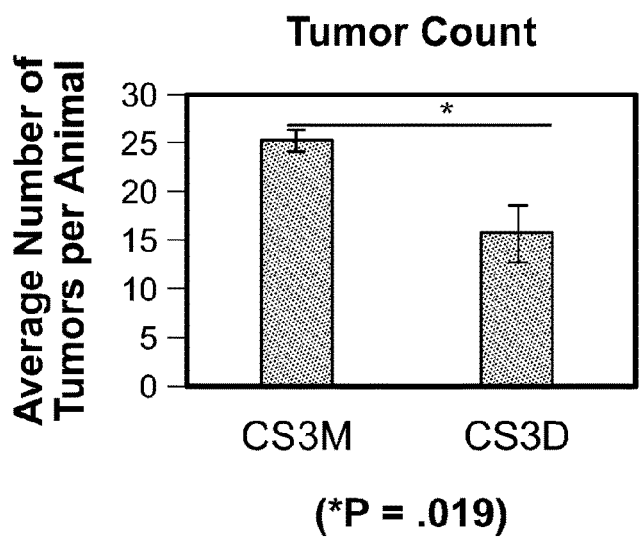
FIG. 15B shows a bar graph of counts of tumors from lungs examined 20 weeks after the end of treatment with CS3M or CS3D, showing a chemopreventive effect. Number of tumors is reduced 42% (P=0.019)

With evidence that CS3D can delay both preneoplasia formation and prenoplasia progression to adenomas after NNK exposure, we assessed tumor burden formation at a later timepoint (20 weeks post-eight weeks of CS3D administration). The average number of tumors per animal was significantly reduced by approximately 40% in CS3D-treated animals as compared to CS3M control group. FIG. 15A shows photographs of the whole lungs with the tumors visible on the lung surface. Arrows point to visible tumors. FIG. 15B shows enumeration of tumors from lungs of 10 mice per group. This difference was significant at P=0.019. These data show that targeting preneoplasia and the transition towards adenomas by STAT3 inhibition with CS3D suppresses tumor formation in an NNK-induced lung cancer model.

Figure 16:
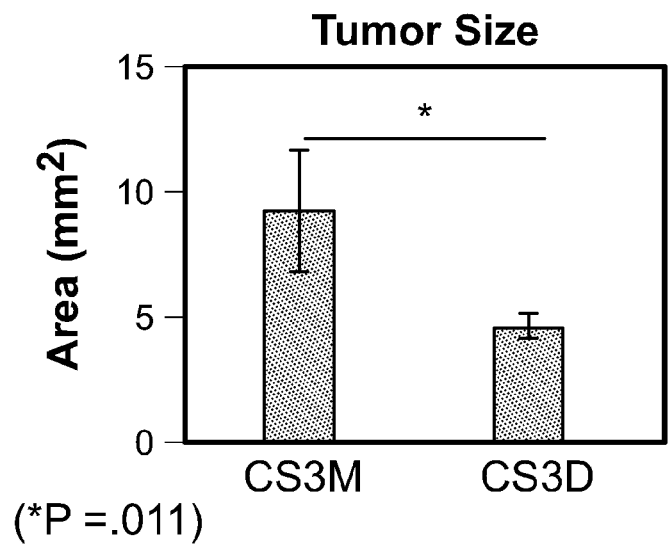
FIG. 16 shows a bar graph of average tumor size after treatment with CS3M or CS3D, 20 weeks after the end of treatment, showing a chemopreventive effect, measured using the LAS V4.12 Leica Imaging program to quantify tumor volumes. Tumor size was reduced 50% by CS3D, showing a chemopreventive effect (P=0.011).

After illustrating that mice treated with CS3D are more resistant to NNK-induced lung preneoplasia and tumor burden formation, tumor size was also determined, by measurements using the LAS V4.12 Leica imaging program measuring individual tumors in each treatment group. CS3D causes 49.8% lower tumor size at 20 weeks post-treatment (FIG. 16), further evidence of the chemoprevention effect.

There was no toxicity observed in mice who received CS3D treatment, based on behavior and weight of the mice and examination of the spleens and livers, suggesting it will be suitable for chemoprevention. Additional details of the method are found in Example 10.

CS3D Effects on Tumor Burden are Independent of K-RAS Mutations

Figure 17:
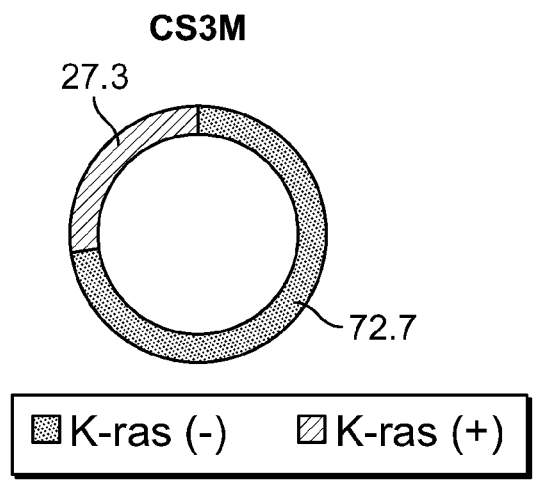
FIG. 17 shows the proportion of KRAS gene G12D mutations (KRAS+) in tumors from mice treated with CS3M or CS3D, 20 weeks after the end of treatment, showing no difference in incidence of KRAS mutations. Tumor tissue was microdissected from individual slides (n=10 for each group) and Sanger sequencing was used to analyze codon 12 of exon 1 of the KRAS gene. The difference was not significant (P>0.1).
Figure 17:
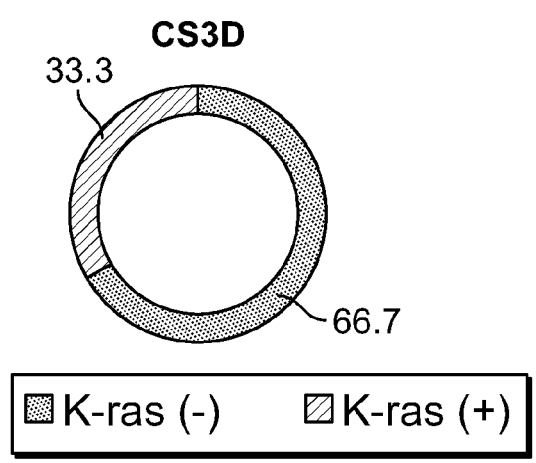

The potential tumor suppressive role of knocking out STAT3 in a K-RAS mutant lung cancer model was recently suggested, and this might mean that a select group of patients who develop K-RAS mutations in the lungs could be less likely to benefit from STAT3-targeted therapy [Grabner et al. Nature Comm. 6:6285, 2015]. This published evidence was generated in a STAT3 knockout mouse model in which no STAT3 protein was expressed. Pharmacological targeting of STAT3 with CS3D was not shown to promote the survival of K-RAS driven tumors in a xenograft model, however (Njatcha et al, Mol. Cancer Therapeutics 17:1917, 2018). To evaluate the percent of tumors positive for K-RAS mutations in the NNK experiment, cells from individual tumors were isolated by laser capture microdissection. Exon 1 of the K-RAS gene was sequenced by Sanger sequencing to determine the presence of the G12D missense genetic mutation which is the K-RAS mutation induced in this strain (FVB/N mice) by NNK. This is the only KRAS mutation known to be produced by NNK in mice. After Sanger sequencing analysis, there was no significant difference in the proportion of tumors positive for K-RAS mutation between CS3D and CS3M control group at tumor that developed 20 weeks post treatment (FIG. 17), P>0.1. These sequencing results demonstrate that pharmacological inhibition of STAT3 with C3SD does not promote the growth of K-RAS mutant lung cancer and should not be an impediment to chemoprevention. This further suggests that smokers (who are likely to have acquired KRAS mutations in their lungs) would be eligible to receive CS3D chemoprevention.

Figure 18:
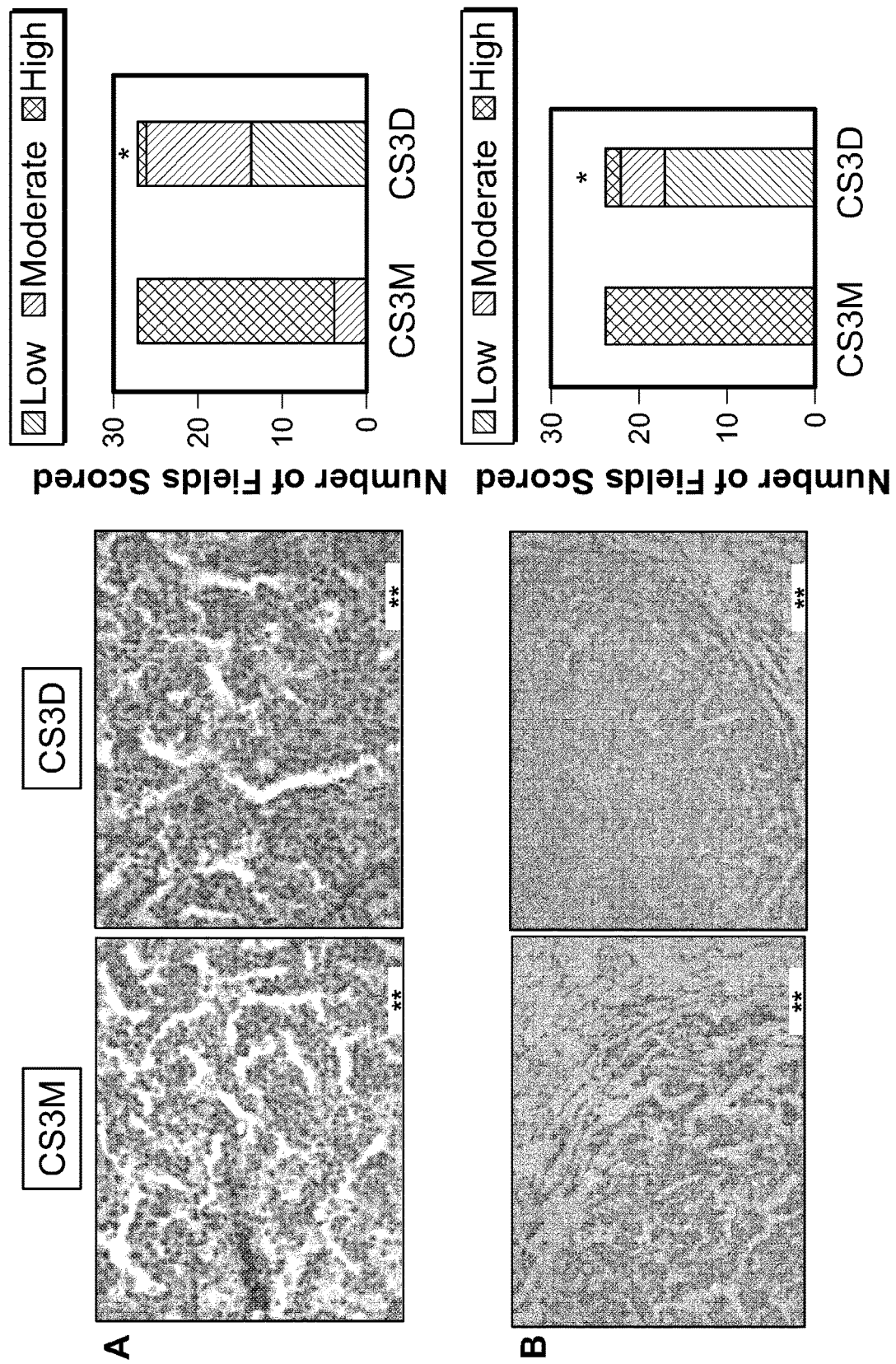
FIG. 18 shows expression of activated phospho-STAT3 protein (Panel A) and activated phospho-NF-Kappa B protein (Panel B) detected by immunohistochemistry in tumors after treatment with CS3M or CS3D, 8 weeks after the end of treatment. Pictures of the stained sections are shown on the left and enumeration of the number of microscopic fields scored low, medium, or high staining is on the right. There is an enrichment of microscopic fields scored low to moderate in CS3D-treated tumors (P<0.05) for both phospho-STAT3 (panel A) and phospho-NFKB (panel B). This further supports ability of C53D to cause p-STAT3 degradation.

STAT3-Induced Degradation by CS3D During Chemoprevention Reduces NF-kB Activation The selective survival of K-RAS driven tumors in a STAT3 knockout system as described by Grabner and colleagues (Nature Comm. 6:6285; 2015) identified an NF-kB escape signaling mechanism. NF-kB promotes the survival of mutant K-RAS clones by promoting an immunosuppressive phenotype that involves blood vessel formation and macrophage infiltration. With knowledge of this potential drug-resistant mechanism, the effects of CS3D on both STAT3 activation and NF-kB activation were assessed. CS3D caused long-term reduction in activated phospho- STAT3 protein at 8 weeks post-treatment in the NNK model (FIG. 18A,P<0.05) consistent with the degradation of STAT3 shown in the previous treatment models. The CS3D-mediated effect is also accompanied by a decrease in phospho-NF-kB activation (FIG. 18B, P<0.05), indicating that CS3D can effectively degrade STAT3 while simultaneously impairing NF-kB (rather than activating) signaling. This finding reinforces the conclusion that even if KRAS mutations are present, the NF-kB signaling system will not be activated by CS3D, producing no effects that would impede chemoprevention in smokers. The long-term loss of pSTAT3 reinforces the claim that CS3D causes STAT3 protein degradation.

CS3D Disrupts the Pro-Tumorigenic Phenotype Associated with Lung Cancer Development STAT3 as a transcription factor has been widely implicated in several oncogenic events that defines the hallmarks of cancer development. Angiogenesis, cell cycle progression, and chronic inflammation are all STAT3 dependent processes that respectively regulate pro-survival factors such as VEGF, MYC and IL-6. Biopsies from smokers at high risk of lung cancer shows that preneoplastic changes in the lungs consist of capillary blood vessels and angiogenic protrusions which helps establish a pattern of microvascularization [Jamicki et al Cell Div. 5:14, 2010]. Contrary to smokers, biopsies from nonsmokers lack those vascularized lesions, suggesting that VEGF-dependent microvascularization at an early stage of lung carcinogenesis is a clinical feature that can be targeted to prevent tumor formation. VEGF activation in the endothelial compartment is known to be partly regulated by STAT3 [Chen et al. Cancer Biol. & Therapy 7:1994, 2008]. Enhanced vascularization in preneoplastic lesions suggests targeting STAT3 might disrupt the NNK-induced pro-tumorigenic angiogerive phenotype.

Figure 19:
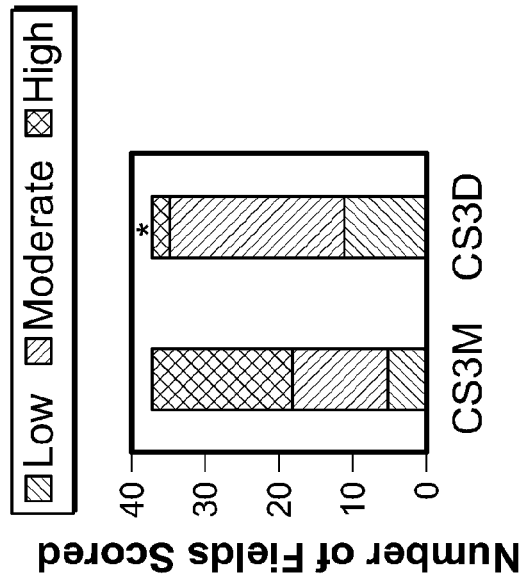
FIG. 19 shows protein expression of the angiogenic marker VEGF in the lungs 8 weeks after the end of treatment period with either CS3M or CS3D, detected by immunohistochemistry. Pictures of the stained sections are shown on the left and enumeration of the number of microscopic fields scored low, medium, or high staining is on the right. There is an enrichment of microscopic fields scored low or moderate in CS3D-treated tumors (P<0.05), showing a reduction in angiogenic stimulation.
Figure 19:
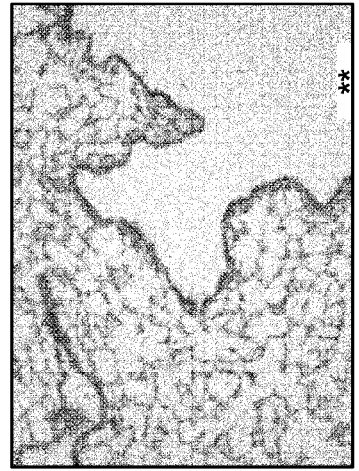
Figure 19:

Immunohistochemical analysis of airways containing preneoplasias at 8 weeks post-treatment caused a decrease in VEGF staining in the airways (FIG. 19, P<0.05). CS3D also suppresses the endothelial marker CD31 expression (data not shown) suggesting that CS3D impairs the degree of angiogenesis at the premalignant stage. This observation further supports the use of CS3D for chemoprevention.

Figure 20:
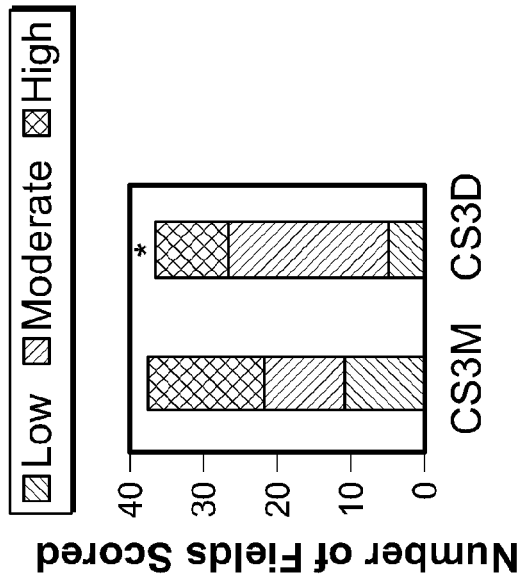
FIG. 20 shows protein expression of the cytokine interleukin 6 (IL-6) in the lungs detected by immunohistochemistry in tumors after treatment with CS3M or CS3D, 8 weeks after the end of treatment. Pictures of the stained sections are shown on the left and enumeration of the number of microscopic fields scored low, medium, or high staining is on the right. There is a decrease in the number of fields scored low with CS3D treatment (P<0.05), indicating IL6 was induced by CS3D.
Figure 20:
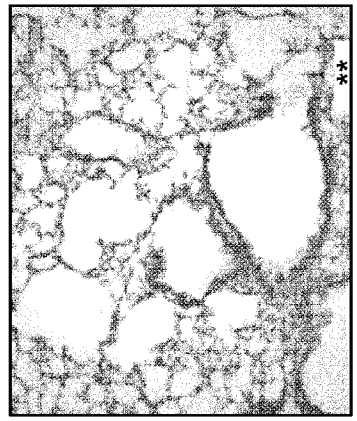
Figure 20:
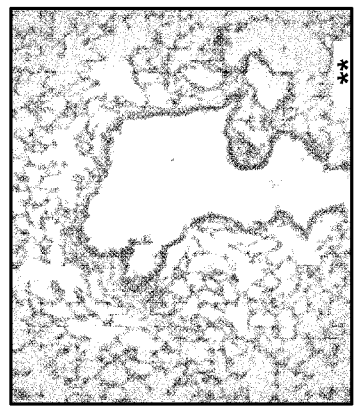

In addition to vascularization, chronic inflammation is now recognized to be important in the pathogenesis of lung cancer. Patients with lung cancer have elevated levels of IL-6 which mediates inflammatory signals via canonical activation of STAT3. Because IL-6 is a major activator of STAT3, inhibition of STAT3 activity by CS3D could deprive cells of downstream IL6 signaling. IL-6 expression was evaluated in response to CS3D and results show that IL-6 levels in the airways are upregulated 8 weeks after completion of therapy with CS3D compared to CS3M, indicating cells may upregulate IL6 production as a rescue mechanism in an attempt to activate STAT3 (FIG. 20, P<0.05). This rebounding effect can be used as a biomarker of CS3D activity in patients, and IL6 measurement in blood, blood products, or other tissues can be used as a biomarker to monitor increased IL6 production, to show whether CS3D is showing biologic activity in patients.

Figure 21:
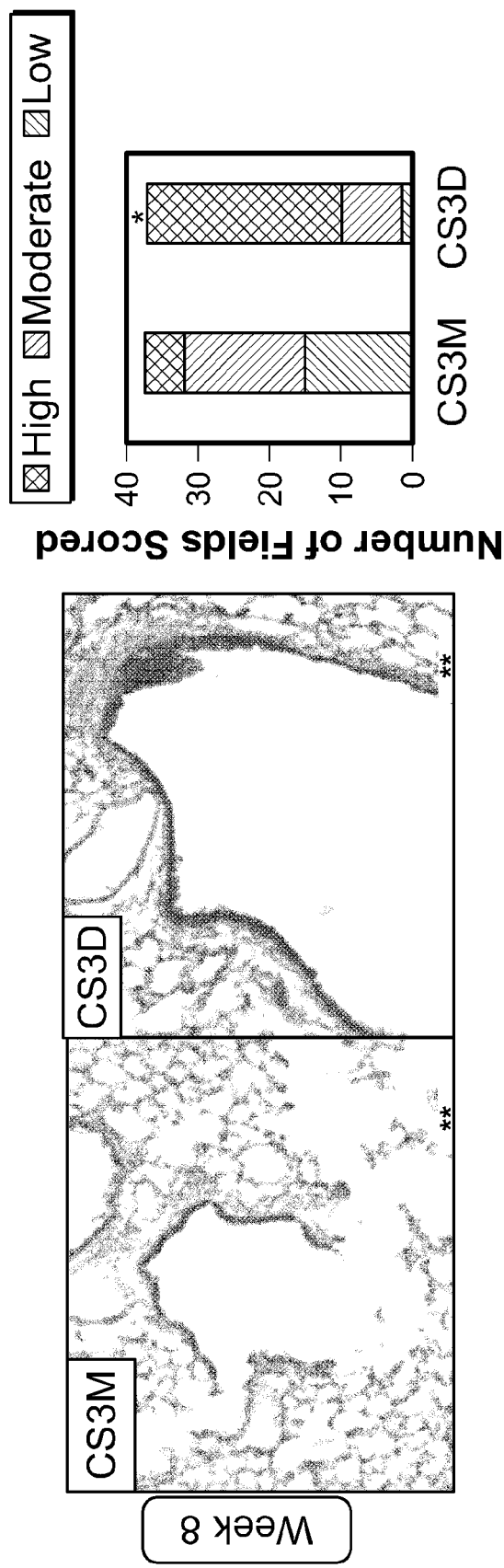
FIG. 21 shows protein expression of the enzyme cyclooxygenase 2 (COX2) in the lungs 8 weeks after the end of treatment with either CS3M or CS3D, detected by immunohistochemistry. Pictures of the stained sections are shown on the left and enumeration of the number of microscopic fields scored low, medium, or high staining is on the right. There is a decrease of microscopic fields scored low in CS3D-treated tumors (P<0.05), indicating COX2 protein was induced by CS3D.

In addition to IL-6 upregulation, STAT3 inhibition by CS3D also mediated a rebounding increase in COX-2 expression (P<0.0001) (FIG. 21). Increased COX-2 protein or pathway activity (such as measuring PGE2, the product of COX2 enzyme in blood, blood products, or tissues) can also be a biomarker for biological activity of CS3D. Because COX2 upregulation can contribute to lung tumorigenesis, combining CS3D with COX inhibitors such as aspirin or ibuprofen might enhance the chemopreventive effect. Both the IL6 and COX2 or COX2 pathway members such as PGE2 can be used as biomarkers for any type of STAT3 Blocker/Degrader.

Figure 22:
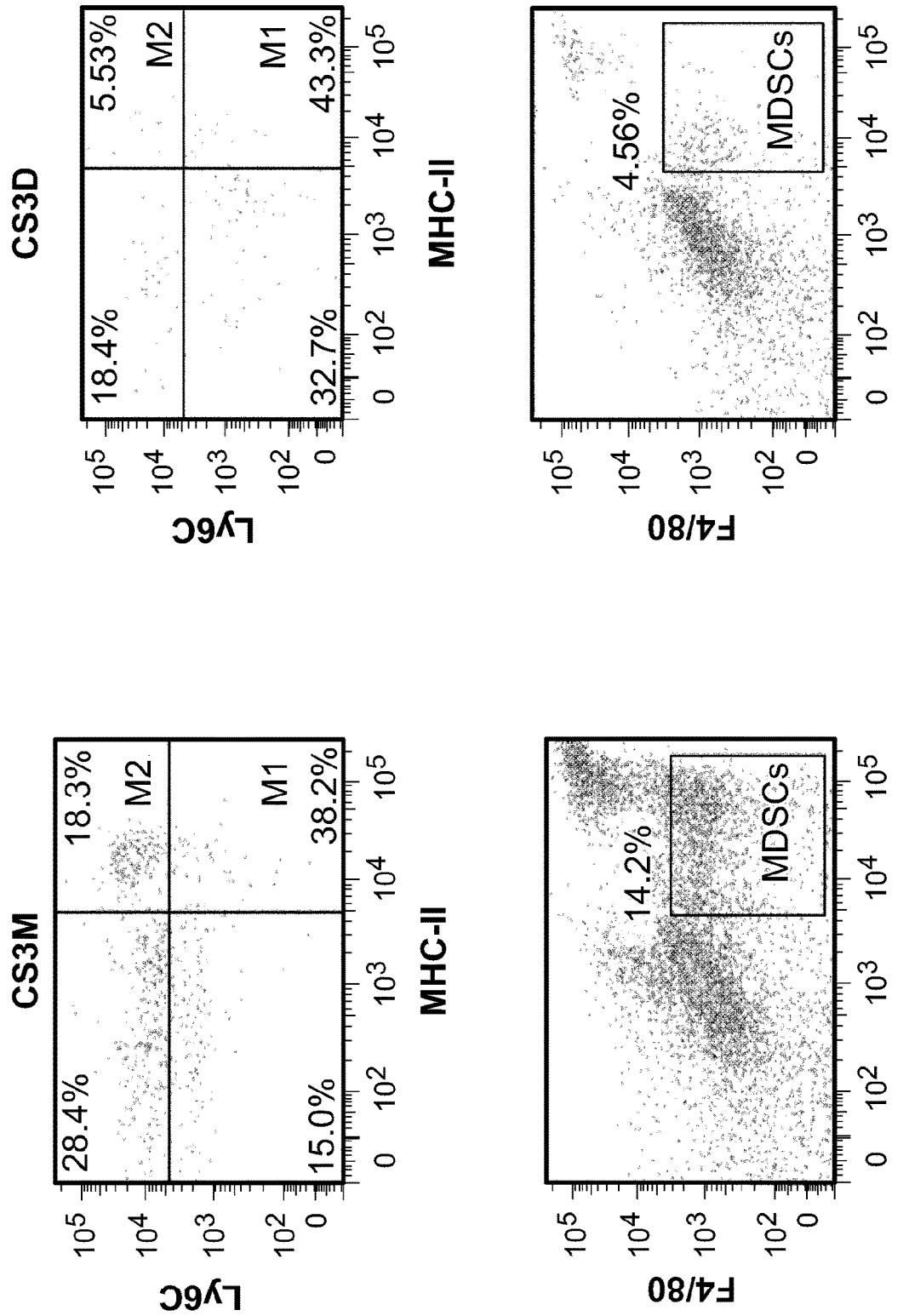
FIG. 22 shows proportion of different immune cell types detected by flow cytometry to separate immune cells removed from lungs of mice treated with NNK for 4 weeks, followed by 1 week of CS3M or CS3D administration. Cells detected are M1 macrophages, M2 macrophages, and MDSCs. The percentage of M2 macrophages and MDSC cells is reduced, while the percentage of M1 macrophages is increased, in CS3D-treated mice, showing a shift towards more anti-tumorigenic immunity with CS3D.

Pharmacological Inhibition of STAT3 by CS3D Shifts the Immunosuppressive Phenotype Towards an Antitumor Immune Response STAT3 also plays a central role in immune evasion. STAT3 specifically orchestrates immunosuppression by promoting M2 macrophage and myeloid-derived suppressor cells (MDSCs) activity while suppressing M1 macrophage function [Su et al. Int. J. Mol. Science 19: pll:E1803, 2018]. Thus STAT3 inhibition by CS3D should favor an antitumor immune response by enhancing M1 macrophage activity. Flow cytometry analysis of cells isolated from the lungs of mice that had first received NNK treatment for 4 weeks followed by 1 week of drug administration revealed that CS3D treatment in mice promotes an antitumor response by increasing the proportion of M1 macrophages present in the lung TME and also decreasing M2 macrophages (5.53% vs. 18.3%) and MDSCs (14.2% vs. 4.56%) (FIG. 22), compared to control CS3M treatment. This indicates that CS3D may reduce immunosuppression as part of the chemopreventive mechanism, and treatment with CS3D in combination with cancer immunotherapy that enhances the anti-cancer activity of any cells of the innate or acquired immune system could improve both its chemopreventive or therapeutic effect.

Pharmaceutical Formulations and Dosage

In one embodiment, the STAT3 Blocker/Degrader is given to a patient multiple times a day for chemoprevention. In another embodiment, the STAT3 Blocker is given to a patient 1 to 7 times per week for chemoprevention. In one embodiment, the course of treatment with the STAT3 Blocker for chemoprevention is between 1 day and 52 weeks. In another embodiment, the course of treatment with the STAT3 Blocker for chemoprevention is 1 to 5 years. In another embodiment, the course of treatment with the STAT3 Blocker for chemoprevention is greater than 5 years. In another embodiment, the course of treatment with the STAT3 Blocker for chemoprevention is for the remaining duration of the patient's natural life. Patients may have multiple courses of treatment. In some embodiments, the patient is given 1 to 100 courses of treatment. In other embodiments the patient is given 101 to 1000 courses of treatment. In still other embodiments, the patient is given more than 1000 courses of treatment.

Individual dosing typically ranges from 0.1 mg/kg to 1000 mg/kg for the STAT3 Blocker. In one embodiment, the individual dose ranges from 0.5-100 mg/kg. In a preferred embodiment, the individual dose ranges from 1-6 mg/kg for the STAT3 Blocker. Dosing may be adjusted for age and cancer risk profile for a given patient.

The STAT3 Blocker compositions of the invention can be formulated as pharmaceutical compositions and administered to a mammalian host, such as a human patient in a variety of forms adapted to the chosen route of administration, i.e., orally or parenterally, by intravenous, inhalation, intramuscular, topical or subcutaneous routes.

Thus, the present compounds may be systemically administered, e.g., orally, in combination with a pharmaceutically acceptable vehicle such as an inert diluent or an edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate: a disintegrating agent such as corn starch, potato starch, alginic acid and the like: a lubricant such as magnesium stearate; and a sweetening agent such as sucrose, fructose, lactose or aspartame or a flavoring agent such as peppermint, oil of wintergreen, or cherry flavoring may be added. The tablet may be coated with a glidant to facilitate passage through the gastrointestinal tract. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenous or intraperitoneal by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form. i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the STAT3 Blocker compositions can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compositions to the skin are known to the art (U.S. Pat. Nos. 4,608,392; 4,992,478; 4,559,157; 4,820,508).

Useful dosages of the compositions can be determined by comparing the in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in chemoprevention will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

STAT3 Blocker/Degrader compositions of the invention can also be administered in combination with other therapeutic agents, for example, other chemotherapeutic agents, including but not limited to selected from erlotinib, afatinib, and osimertinib; and/or other chemoprevention agents such as aspirin, ibuprofen, anti-oxidants, iloprost, or drugs of the glitazone class such as pioglitazone: and/or in combination with agents that activate anti-tumor is immunity such as immune checkpoint blockers like pembrolizumab or nivolumab.

EXAMPLES

Antibodies and Reagents: Antibodies for STAT3, phospho-STAT3, p-NFKB, cyclin DI, cleaved caspase-3 (CC3), c-Myc, Ki67, GAPDH, Ubiquitin and horseradish peroxidase-conjugated secondary antibodies were purchased from Cell Signaling Technology (Danvers, Massachusetts). The CellTiter 96 AQ. One Solution (MTS) Reagent containing a tetrazolium compound [3-(4,5-dimethylthiazol-2-yl)-5-(3-carboxymethoxyphenyl)-2-(4-sulfophenyl)-2H-tetrazolium was obtained from Promega (Madison, Wisconsin).

Cell Culture: The wild-type EGFR (201T) cell line was derived from a patient with lung adenocarcinoma as described previously (Siegfried J M, et al, *Pulm Pharmacol Ther* (1999) 12:291-302). H1975 cells with the EGFR intrinsic point mutation L858R and the acquired EGFRi resistance mutation T790M were purchased from American Type Culture Collection (Manassas, Virginia). 201T and H1975 were cultured in BME and RPMI respectively containing 10% heat-inactivated fetal bovine serum and 1× penicillin/streptomycin (Thermo Fisher, Waltham, Massachusetts) and 1× GlutaMax (Life Technologies, Carlsbad, California) maintained at 37° C. with 5% CO2. Other cell lines were purchased from ATCC (A549 and H3255) cultured in BME and RPMI, respectively. Human bronchial epithelial cells were purchased from ATCC, and primary normal lung fibroblasts were derived from human lung tissue (Stabile L P, et al, *Cancer Res* (2002) 62:2141-50). Cell lines were authenticated by short tandem repeat DNA profiling.

Example 1 Cyclic STAT3 Decoy (CS3D) Transfections

The single-stranded STAT3 decoy and inactive mutant version were generated as previously described (Klein J D, et al, *PLoS One PLoS ONE* (2014) 9(1): e81819. doi: 10.1371/journal.pone.0081819): Siegfried J M, et al, *Pulm Pharmacol Ther* (1999) 12:291-302). The inactive single-stranded mutant version differs by a base-pair at position 9 (G to T) as compared to the STAT3 decoy. Both oligonucleotides were synthesized by Integrated DNA Technologies (IDT) by phosphoramidite chemistry on solid-phase. The single-stranded oligonucleotide (sense and antisense strands) was further modified with two hexaethyleneglycol linkers attached to both strands, allowing the structure to circularize upon enzymatic ligation of the 3' and 5' ends of the annealed oligonucleotide. Both molecules were purified by HPLC according to manufacturer's modifications and reports (IDT). Using T4 DNA ligase (New England Biolabs, Ipswich, Massachusetts), ligations were performed overnight to produce the cyclic STAT3 decoy (CS3D) and the inactive circularized mutant control version (CS3M). Ligation efficiency was analyzed on a 15% TBE gel and it ranged between 85 to 95%, showing that amount of the cyclic form predominates over the linear form of the STAT3 decoy (CS3D) and the mutant construct (CS3M). The linear form is also less stable, and is less likely to contribute to the biological effects in the presence of an excess of the cyclic form.

Fluorescently-labeled CS3M and CS3D (with iFluor) were also produced using enzymatic ligation as described above and used to assess uptake efficiency. Transfections of the cyclic oligonucleotides were performed using Lipofectamine 2000 (Life Technologies) in opti-MEM media (Life Technologies) as follows: Cells were plated at 75-800% confluency, and exposed to transfection media containing the respective circularized oligonucleotides for 24 hours at 37° C. Post-transfection, cell recovery was initiated in media containing 10% heat-inactivated fetal bovine serum.

Example 2 MTS Assays and Programmed Cell Death Analysis

Dose-response experiments assessing the relative number of metabolically active viable cells were performed by transfecting cells with increasing concentrations of CS3D or CS3M, followed by performance of MTS assays. After 72 hours, 5 mg/ml of MTS reagent was added in the plates and incubated 37° C. for 20 minutes. The plates were then read at 490 nm in a Synergy microplate reader (BioTek, Winooski, Vermont) using Gen5 2.05 software. Data obtained following treatment with C3SD or CS3M were normalized to treatment with lipofectamine alone. $IC_{50}$s determined from these experiments were used to perform independent assays to confirm the effects of CS3D relative to CS3M. To assess induction of apoptosis in response to CS3D, H1975 and 201T cells were transfected with 100 nM of CS3M or CS3D. After twenty four hours of transfection, cells were resuspended in annexin V-binding buffer, incubated with 5 µL of propidium iodide (BD Biosciences) and subjected to flow cytometric analysis, using a BD FACS Canto II Flow Cytometer.

Example 3 Colony Forming Assays

Following the transfection protocol described above, cells transfected with either CS3D or CS3M were detached from the plate using Trypsin-EDTA (Life Technologies) and seeded at a density of $2 \times 10^4$ cells/well (in a 6-well plate) in soft agar to determine the ability of cells to grow in an anchorage-independent setting. Sea Plaque Agarose (Lonza—Rockland, Maine) was used to prepare 0.8% base agarose layer and a 0.48% upper agarose layer containing the transfected cells. 1 ml of appropriate growth media was added into each well and incubated at growth conditions of 37° C. with 5% $CO_2$. Media was replaced every 3-4 days and colony formation was monitored. After 15-20 days, the media was aspirated, and wells were incubated with crystal violet in 10% formalin for 1 h. Using a dissecting scope, colonies were photographed in a 6-well plate (with 4 quadrants/well) using ImageJ software analysis to automatically count colonies, using 35 pixels as a cut-off.

Example 4 Immunoblotting

Cells were seeded at $0.5 \times 10^6$ cells/well in six-well plates in BME/RPMI containing 10% FBS and transfected with 0.1 µM CS3D/CS3M for 24 hours as described above. Post-transfection, cell lysates were extracted, and protein concentrations quantified using DC assay reagents. Whole cell lysates (20 micrograms/sample) were electrophoresed on 7.5% SDS-polyacrylamide gels for 1 h and transferred onto Trans-Blot polyvinylidene difluoride (PVDF) membranes (Bio-Rad Laboratories) for 1 h at 100 V. The membranes were blocked using 5% nonfat dry milk, 0.1% Tween 20 in 1× phosphate-buffered saline (TBST) for 1 h. Membranes were incubated in primary antibody diluted at 1:1000 at 4° C. overnight, and washed three times with TBST (15 min/wash). The membranes were then incubated with secondary antibody for 1 h (1:2000) at room temperature, followed by three washes in TBST. Blots were later developed using a super-enhanced chemiluminescence substrate according to the manufacturer's protocol (ThermoScientific). ImageJ 1.X software was used to quantify the results and assess changes in protein expression patterns.

Example 5 Confocal Microscopy

Twenty-four hours post-transfection with fluorescein-tagged CS3D, H1975 cells were fixed in 4% paraformaldehyde and prolong antifade reagent (CST) was applied directly to the slides. Fixed cell imaging was performed using a Nikon Eclipse Ti Confocal Microscope System. Images were captured and analyzed using the imaging software NIS Elements and Image J. Fluorescence detection of fluorescein-labelled CS3D was detected at 488 nm. Images were taken and processed at 40× and 60×.

Example 6 Immunoprecipitation (IP)

Post-transfection with either 100 nM CS3D or CS3M, H1975 were lysed in IP lysis buffer (Thermo Scientific, Rockford, Illinois) supplemented with protease inhibitor cocktail (Roche, Basel, Switzerland) and phosphatase inhibitors (NaF and Na3VO4). Immunoprecipitations were performed using the appropriate antibody (pSTAT3) at 1:500 and Protein A Magnetic Beads (Thermo Scientific) at 4° C. Immunoprecipitated lysates were electrophoresed on 7.5% SDS-polyacrylamide gels followed by exposure to ubiquitin (1:1000) at 4° C. overnight and the appropriate secondary antibody while following the immunoblotting method described above.

Example 7 Real-Time qPCR

Post transfection, cells were treated with 10 ng/ml EGF for 1.5 hr to activate STAT3. Trizol (Invitrogen, Carlsbad, California) was then used to extract total RNA. One microgram of total RNA was reverse-transcribed using a cDNA synthesis kit (Quanta Biosciences) according the manufacturer's instructions using a T100 Thermal Cycler (BioRad). Real-time qPCR (polymerase chain reaction) was performed using a SYBR Green Super Mix kit on a CFX connect Real-Time System (BioRad). Gene-specific DNA oligonucleotide primers for STAT3 target genes were used to assess mRNA levels normalized to GAPDH mRNA levels as internal control, and the ratio of normalized mRNA to the control conditions was determined using the comparative ΔCT method for analysis. The primers used for real-time qPCR are as follows:

```
Bcl-xL forward
                                        SEQ ID NO.: 7
5'-ATGCAGGTATTGGTGAGTCG-3'

Bcl-xL reverse
                                        SEQ ID NO.: 8
5'-CTGCTGCATTGTTCCCATAG-3'

GAPDH forward
                                        SEQ ID NO.: 9
5'-GGA GCG AGA TCC CTC CAA
AAT-3'

GAPDH reverse
                                        SEQ ID NO.: 10
5'-GGC TGT CAT ACT TCT CAT
GG-3'
```

```
-continued
IL-6 forward
                                        SEQ ID NO.: 11
5'-ACT CAC CTC TTC AGA ACG
AAT TG-3'

IL-6 reverse
                                        SEQ ID NO.: 12
5'-CCA TCT TTG GAA GGT TCA
GGT TG-3' c-MYC forward
                                        SEQ ID NO.: 13
5' CCGCATCCACGAAACTTTG-3' c-MYC reverse
                                        SEQ ID NO.: 14
5'- GGGTGTTGTAAGTTCCAGTGCAA-
3'
```

Example 8 In Vivo Tumor Xenograft Studies

All studies were approved by the University of Minnesota Institutional Animal Care and Use Committee and were carried out in accordance with institutional guidelines for animal care. Female nude mice (4-6 weeks old) were injected with $1 \times 10^6$ cells in the flanks. After 3 weeks, animals with palpable tumors (200 mm$^3$) were randomized into two treatment groups with 10 tumors/group. Daily tail vein injections (5 days per week) of the cyclic STAT3 decoy (CS3D) or mutant STAT3 control (CS3M) (100 µg in 200 µl per injection) was delivered for 2-3 weeks. Tumor measurements were made with calipers every 2 days. Volumes were calculated from the formula $V=(Length \times Width^2)/2$. After treatment, the animals were sacrificed according to IACUC guidelines.

Immunohistochemical analysis: Tumors were excised for immunohistochemical (IHC) staining; 5-µm (micron) sections were cut from formalin-fixed paraffin-embedded tissue blocks, deparaffinized and rehydrated using successive washes of xylene followed by ethanol. Antigen retrieval was performed in a microwave oven (for 20 minutes) in an unmasking solution containing sodium citrate buffer followed by peroxidase blocking in 3% hydrogen peroxide. The sections were incubated in ABC blocking buffer (Vector laboratories Inc, Burlingame, California) for 1 hour at room temperature. Sections were then stained with H&E (hematoxylin and eosin) or subjected to sequential incubations with different primary antibodies and peroxidase-conjugated goat anti-rabbit secondary antibodies. The following primary antibodies were used (at the indicated dilutions): cleaved caspase-3 (#9664, Cell Signaling, 1:300), p-STAT3 (#9145, Cell Signaling, 1:400), Ki67 (#ab15580, Abcam, 1:1000). Sections were developed with DAB and counterstained with hematoxylin. Bright field microscopy was performed using Leica DM 4000 B LED microscope and images were captured at 20× and 40× magnification using LASv4.7 software. IHC analysis was done as a blinded study with 100 images from each treatment group graded as low, moderate, or high. Staining was graded as low (<30% positive cells per field, scored as 1), moderate (30-60% positive cells per field, scored as 2) or high (>60% positive cells per field, scored as 3).

Statistical Analyses: For statistical analyses, data were reported as mean standard deviation (SD) or standard error of the mean (SEM). To assess significance between different treatment groups, a student's t test (two tailed) was used to determine significance with p values at least <0.05 categorized as statistically significant. To analyze IHC scoring data, Chi-Squared test was used to compare the frequency of scores of 1,2, or 3 in treatment groups.

Example 9 In Vivo Orthotopic NSCLC Tumor Growth

NSCLC cells are injected by tail vein into scid (severe combined immunodeficiency) mice, using cells tagged with a LUC vector that are suspended in saline with 15% Matrigel. NSCLC cell lines to be examined are 201T, H1975 and A549 from Table 1, as well as H23, which is EGFR WT/KRAS G12C mutant. Following 1 wk (week) for engraftment, tumor growth will be monitored by bioluminescence. Placebo or HER TKI is then given by gavage and STAT3 decoys (CS3D and CS3M) are administered by IV injection 5 days per week, for 14-21 days, depending on response. Groups will be vehicle alone, afatinib (GILOTRIF®, Boehringer Ingelheim) alone (25 mg/kg [standard dose]), CS3D alone (5 mg/kg), CS3M alone (5 mg/kg), afatinib combined with CS3D and afatinib combined with CS3M. In addition to imaging, lung tumors are also assessed at sacrifice histologically and by IHC (in formalin fixed paraffin embedded tissues[FFPE]) and by immunoblotting of frozen unfixed lysates after sacrifice (2 lung lobes are set aside from each mouse to prepare lysates). All animal procedures are in accordance with IACUC guidelines and approval. Doses will be adjusted if needed for each cell line. Mice are monitored for weight, activity level, and breathing difficulty. For therapy studies, 8 animals per group will give 80% power at p=0.05 to detect a mean >25% effect size, based on 20% variation among animals. 10 animals/group will be injected to account for average 80% tumor engraftment. An equal number of male and female mice will be used as the host animal.

After determining which orthotopic model responds to CS3D and whether combination with an EGFR TKI is efficacious, lung cancer PDXs, available from Jackson Laboratories, may be used. PDXs with and without EGFR mutation (including #TM00204 with an T790M resistance mutation) and with KRAS mutations if applicable (such as J000095635) will be propagated as subcutaneous xenografts (8 per group) and optimal drug regimen will be tested compared to controls, with tumor size monitored with calipers and signaling evaluation.

Monitoring uptake of CS3D into orthotopic tumors will be done with spiking of FITC-conjugated CS3D (0.5 mg/kg) along with unlabeled CS3D in a separate set of 10 tumor-bearing animals. Accumulation of CS3D is examined by fluorescent microscopy of lungs, livers and spleens from 2 animals collected at 0 time and 1 hr after daily injections on days 1-5 to estimate tissue accumulation after 1-5 doses.

Assessment of signaling molecules: total/phospho-STAT3, total/phospho-EGFR/HERs, total/phospho-NFκB (NF-kappa B), total/phospho MAPK and AKT, as well as protein levels of cyclin D1, Myc, VEGF, IL6 and IL8, and caspase 3 (for apoptosis) will be measured by IHC and/or immunoblotting in tumor lysates. Proliferation index will be assessed by Ki67 labeling. Angiogenesis will be assessed by CD31 IHC staining. EMT/invasion: ECadherin and Snail will be assessed by IHC for EMT; CD44 and focal adhesion kinase (FAK) activation using p-FAK antibody will be assessed to determine invasion. If reduced effects on EMT or invasion are seen this will then be examined after 5 days of CS3D, to determine if reduced EMT/invasion precedes growth effects.

Mean and median tumor volumes based on bioluminescence will be calculated over time of treatment and compared by ANOVA followed by t-test. Significance will be at $P<0.05$. For IHC, scoring will be done on a 1-3 scale (low, medium, high) as previously published (Siegfried et al., $Oncotarget$ (2017) 8:24063-76). FFPE sections from 5 tumors/treatment group will be analyzed, with 20× fields/section (100 total) scored blindly and compared by ANOVA followed by t-test. Positive controls (tumors with known staining) and negative controls (leaving out primary antigen) will be done. For western blotting, individual lysates for 5 tumors/group will be run in duplicate with results normalized for GAPDH or actin. Positive control will be cell lysates known to express protein studied.

Alternate approach: Osimertinib (TAGRISSOR®, AstraZeneca) is a HER TKI developed to treat NSCLC with the EGFR T790M resistance mutation and overcomes the inability of erlotinib to bind to the ATP binding pocket with the T790M alteration. Data suggests that EGFR WT cells are also more sensitive to osimertinib than to erlotinib. Combination therapy by in vitro and in vivo combination index studies with osimeritinib and CS3D may be conducted in selected cell lines to detect and measure synergy.

Example 10 In Vivo NNK-Induced Lung Tumor Model for Chemoprevention

The chemopreventive effect of CS3D compared to CS3M on lung tumor development was studied in an NNK-induced immunocompetent lung tumor model using the tobacco carcinogen, 4-(methylnitrosamino)-1-(3-pyridyl)-1-butanone, CAS Reg. No. 64091-91-4 (NNK) in mice. The advantages of this model are: NNK is an inducer of KRAS mutations, it is known to induce lung cancers in mice and humans, and the model is immunocompetent. In addition, this is a useful model for studying chemoprevention after exposure to a carcinogenic agent (Hecht S S, et al, $Cancer Res.$ (1980) 40(2):298-302).

After four weeks of NNK exposure, mice are then dosed IV 2 times per week with CS3D or CS3M (5 mg/kg) for eight weeks. The mice are sacrificed after at one week, 8 weeks, and 20 weeks after the end of oligonucleotide dosing to examine lungs. Lungs are formalin-inflated and surface tumors are enumerated visually under a dissecting microscope. The area of each tumor is measured with a analysis tool built in the imaging software LAS v4.7 (Leica). Lungs are also sectioned and examined histologically by hematoxylin and eosin staining for counting the preneoplasia and tumors.

Immunohistochemistry is performed on the lung section to determine the expression levels of p-STAT3, P-NFkB, VEGF, IL-6 and COX2. For this 5 µm thick FFPE sections are deparaffinized in xylene and rehydrated in alcohol. Heat mediated antigen retrieval is performed in citrate buffer pH 6.0. The tissue is blocked for nonspecific binding by incubating in 10% goat serum. The tissues sections are incubated with primary antibodies (pSTAT3; 1:400, COX2; 1:600 Cell Signaling), IL-6 (1:600; hermoscientific) VEGF (1:400 Abcam), pNFkB (1:500) Abcam). The primary antibody binding is determined by incubating with HRP conjugated secondary antibody and color developed by incubating the samples in DAB and counter stained with haemotoxylin. The bright field images are captured at 20× or 40× using Leica DM 4000B LED microscope equipped with LASv407 software. Staining is graded as low (<30% positive cells per field score 1, moderate (30%-60% positive cells per field, scored as 2), or high (>60% positive cells per field, scored as 3).

In order to determine the KRAS status of individual tumor, 10 um FFPE lung sections are mounted on special Leica foiled glass slides. Sections are stained with H&E and slides are mounted on Laser captured Microdissection (LCM) stage of LMD6500 laser microdissection microscope. Desired tumor sections are microdissected and captured in labeled tubes. Total DNA is isolated using DNA isolation kit (Qiagen). To amplify exon 1 that contains codon 12/13, 50 ng of DNA sample was used for the PCR amplification reaction in a final 25 μL volume containing 1×GoTaq Green Master Mix (12.5 μL) (Promega), 0.2 μM each of the pair of primers (forward: 5'-GACATGTTCTAATTTAGTTG-3' (SEQ ID NO: 18); reverse: 5'-AGGCGCTCTTGCCTACGGCA-3' (SEQ ID NO: 19)) [153], and nuclease-free water to 25 μL. The mixture was heated at 95° C. for 9 minutes then subjected to 40 cycles (94° C./1 min, 53° C./1 min, 72° C./1 min). For the $2^{nd}$ round PCR, 1 μL of the first round PCR products was then diluted into a final 25 μL with same reaction buffer but amplified with a different set of primers (forward: 5'GCCGCCTGCAGCCCGCGCCCCCGTGCCCCCGCCCCGCCGCCGGCCCGGCGCCCT ATTGTAAGGCCTGCTGAAAAT-3' (SEQ ID NO: 20); reverse: 5'-AGGCGCTCTTGCCTACGGCA-3' (SEQ ID NO: 19)) [153]. The $2^{nd}$ reaction was heated at 95° C. for 9 min then subjected to 25 PCR cycles (94° C./1 min, 60° C./1 min, 72° C./1 min). The PCR products containing the 126 bp exon 1 fragment were then sequenced (Sanger) and analyzed for the G12D substitution mutation using ExPASy Translate tool.

Example 11 Flow Cytometry on the Cells Isolated from the Lungs from CS3M and CS3D Mice Lungs from mice were digested with RPMI media containing collagenase and DNase to obtained single cell suspension. The cells were counted and 1×10$^6$ cells were staining with fluorescent labeled CD45, CD11b, MHC II, Ly6C and F4/80. The labeled cells were gated and data acquired on LSR fortessa (BD Biosciences) and further analysed by Flowjo.

Example 12 Representative Pharmaceutical Formulations and Dosage Forms as Tablets, Capsules, Parental Injection, and Aerosol, Containing a Compound of Formula I, for Therapeutic or Prophylactic Use in Humans

| (i) Tablet 1 | mg/tablet |
|---|---|
| STAT3 compound | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 total |

| (ii) Tablet 2 | mg/tablet |
|---|---|
| STAT3 compound | 20.0 |
| Microcrystalline cellulose | 410.0 |
| Starch | 50.0 |
| Sodium starch glycolate | 15.0 |
| Magnesium stearate | 5.0 |
| | 500.0 total |

| (iii) Capsule | mg/capsule |
|---|---|
| STAT3 compound | 10.0 |
| Colloidal silicon dioxide | 1.5 |
| Lactose | 465.5 |
| Pregelatinized starch | 120.0 |
| Magnesium stearate | 3.0 |
| | 600.0 total |

| (iv) Injection 1 (1 mg ml) | mg/ml |
|---|---|
| STAT3 compound | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| STAT3 compound | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| STAT3 compound | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations are only representative and may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for the prevention of lung cancer by administering to a patient in need or at risk a therapeutically-effective dose of a STAT3 Blocker/Degrader, wherein the STAT3 Blocker is a CS3D oligonucleotide having the structure:

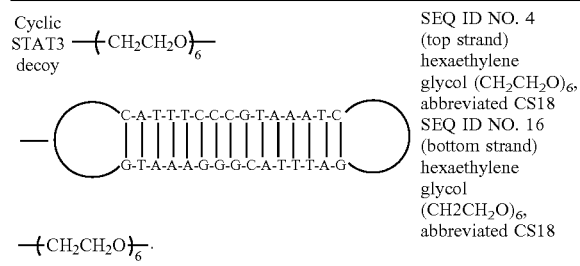

| | |
|---|---|
| Cyclic STAT3 decoy —(CH₂CH₂O)₆— <br><br> —(CH₂CH₂O)₆—. | SEQ ID NO. 4 (top strand) hexaethylene glycol (CH₂CH₂O)₆, abbreviated CS18 <br> SEQ ID NO. 16 (bottom strand) hexaethylene glycol (CH2CH₂O)₆, abbreviated CS18 |

2. The method of claim 1 wherein the STAT3 Blocker modulates phosphorylated STAT3.

3. The method of claim 1 wherein the therapeutically-effective dose of a STAT3 Blocker is administered to the patient for chemoprevention of non-small cell lung cancer.

4. The method of claim 1 wherein the patient is at elevated risk of developing cancer, due to one or more factors selected from a genetic condition, immunocompromised status, comorbidities, prior treatment for cancer, incidence of cancer, prior treatment with or exposure to one or more chemotherapeutic agents, radiation therapy, exposure to radiation or radon, prior exposure to or treatment with one or more carcinogenic or cytotoxic agents, and social or family history correlated with the incidence of cancer.

5. The method of claim 4 wherein the patient has been exposed to asbestos;

or is or has been a smoker.

6. The method of claim 1 wherein the oligonucleotide comprises one or more internucleotide phosphate analogs, selected from phosphorothioate, phosphoramidate, and alkylphosphonate, or one or more locked nucleic acid (LNA) nucleoside analogs.

7. The method of claim 1 wherein the oligonucleotide is a cyclic oligonucleotide.

8. The method of claim 1 wherein the oligonucleotide comprises SEQ ID NO.:5 where (CS18) is a hexaethyleneglycol, —(CH₂CH₂O)₆ spacer.

* * * * *

SEQUENCE LISTING

<160> NUMBER OF SEQ ID NOS: 20

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catttcccgt aaatc                                                     15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatttacggg aaatg                                                     15

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catttcccgt aaatcgaaag atttacggga aatg                                34

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
catttcccgt aaatc                                                     15

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatttacggg aaatgcscat ttccc                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatttaaggg aaatgcscat ttccc                                          25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgcaggtat tggtgagtcg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgctgcatt gttcccatag                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggagcgagat ccctccaaaa t                                               21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggctgtcata cttctcatgg                                                 20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actcacctct tcagaacgaa ttg                                             23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatctttgg aaggttcagg ttg                                             23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgcatccac gaaactttg                                                  19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggtgttgta agttccagtg caa                                             23

<210> SEQ ID NO 15
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(50)
<223> OTHER INFORMATION: a, c, t or g
<220> FEATURE:
<221> NAME/KEY: misc_feature
<222> LOCATION: (1)..(50)
<223> OTHER INFORMATION: This region may encompass 0-50 nucleotides
<220> FEATURE:
<221> NAME/KEY: modified_base
<222> LOCATION: (53)..(53)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (61)..(61)
<223> OTHER INFORMATION: a, c, t or g
<220> FEATURE:
<221> NAME/KEY: modified_base
<222> LOCATION: (63)..(63)
<223> OTHER INFORMATION: a, c, t or g
<220> FEATURE:
<221> NAME/KEY: modified_base
<222> LOCATION: (66)..(115)
<223> OTHER INFORMATION: a, c, t or g
<220> FEATURE:
<221> NAME/KEY: misc_feature
<222> LOCATION: (1)..(50)
<223> OTHER INFORMATION: This region may encompass 0-50 nucleotides

<400> SEQUENCE: 15
nnnnnnnnnn nnnnnnnnnn nnnnnnnnnn nnnnnnnnnn nnnnnnnnnn canttcncgt     60
nantcnnnnn nnnnnnnnnn nnnnnnnnnn nnnnnnnnnn nnnnnnnnnn nnnnn         115

<210> SEQ ID NO 16
<211> LENGTH: 15
<212> TYPE: DNA
<213> ORGANISM: Artificial Sequence
<220> FEATURE:

<223> OTHER INFORMATION: Description of Artificial Sequence: Synthetic
     oligonucleotide

<400> SEQUENCE: 16
gatttacggg aaatg                                                   15

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 17
ggtgcatcga tgcagggggg                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 18
gacatgttct aatttagttg                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 19
aggcgctctt gcctacggca                                              20

<210> SEQ ID NO 20
<211> LENGTH: 76
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 20
gccgcctgca gcccgcgccc cccgtgcccc cgccccgccg ccggcccggc gccctattgt    60
aaggcctgct gaaaat                                                   76